United States Patent
Shelton, IV et al.

(10) Patent No.: US 10,172,617 B2
(45) Date of Patent: Jan. 8, 2019

(54) MALLEABLE BIOABSORBABLE POLYMER ADHESIVE FOR RELEASABLY ATTACHING A STAPLE BUTTRESS TO A SURGICAL STAPLER

(71) Applicant: Ethicon Endo-Surgery, LLC, Guaynabo, PR (US)

(72) Inventors: Frederick E. Shelton, IV, Hillsboro, OH (US); Rao S. Bezwada, Whitehouse Station, NJ (US); Jason L. Harris, Lebanon, OH (US); Prudence A. Turner, Independence, KY (US); Mark S. Zeiner, Mason, OH (US); Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 541 days.

(21) Appl. No.: 14/667,874

(22) Filed: Mar. 25, 2015

(65) Prior Publication Data

US 2016/0278775 A1  Sep. 29, 2016

(51) Int. Cl.
*A61B 17/10* (2006.01)
*A61B 17/072* (2006.01)
(Continued)

(52) U.S. Cl.
CPC .......... *A61B 17/105* (2013.01); *A61B 17/068* (2013.01); *A61B 17/07292* (2013.01); *A61L 24/046* (2013.01)

(58) Field of Classification Search
CPC ................ A61B 17/105; A61B 17/068; A61B 17/07292; A61L 24/046
(Continued)

(56) References Cited

U.S. PATENT DOCUMENTS

| | | | |
|---|---|---|---|
| 2,642,375 A | * | 6/1953 | Bloch ..................... A61L 15/26 424/426 |
| 4,805,823 A | | 2/1989 | Rothfuss |
| | | | (Continued) |

FOREIGN PATENT DOCUMENTS

| | | |
|---|---|---|
| EP | 1 064 883 A1 | 1/2001 |
| EP | 2 759 269 A1 | 7/2014 |
| EP | 2759269 A1 * | 7/2014 ....... A61B 17/07292 |

OTHER PUBLICATIONS

Extended European Search Report dated Jun. 1, 2016 for Application No. 16162064.6, 9 pages.
(Continued)

*Primary Examiner* — Hemant M Desai
*Assistant Examiner* — Valentin Neacsu
(74) *Attorney, Agent, or Firm* — Frost Brown Todd LLC

(57) ABSTRACT

A surgical stapler end effector comprises a staple cartridge, an anvil, and a buttress assembly. The staple cartridge comprises a plurality of staples and a deck. The staple cartridge is operable to drive the staples through the deck. The anvil is movable from an open position toward the staple cartridge to reach a closed position. The anvil includes an underside having staple forming surface configured to receive staples driven through the deck. The buttress assembly comprises a buttress body and an adhesive material. The adhesive material is configured to removably secure the buttress body to the deck of the staple cartridge or the underside of the anvil. The adhesive material comprises a malleable bioabsorbable polymer.

19 Claims, 28 Drawing Sheets

(51) Int. Cl.
  *A61L 24/04* (2006.01)
  *A61B 17/068* (2006.01)
(58) Field of Classification Search
  USPC .......................................... 227/175.1, 176.1
  See application file for complete search history.

(56) References Cited

U.S. PATENT DOCUMENTS

| | | | |
|---|---|---|---|
| 5,415,334 A | 5/1995 | Williamson et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,325,810 B1* | 12/2001 | Hamilton | A61B 17/07207 227/175.1 |
| 6,364,888 B1 | 4/2002 | Neimeyer et al. | |
| 6,503,257 B2 | 1/2003 | Grant et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,573,461 B2 | 11/2013 | Shelton et al. | |
| 8,573,465 B2 | 11/2013 | Shelton | |
| 8,584,920 B2 | 11/2013 | Hodgkinson | |
| 8,602,288 B2 | 12/2013 | Shelton et al. | |
| 8,616,431 B2 | 12/2013 | Timm et al. | |
| 8,820,605 B2 | 3/2014 | Shelton | |
| 8,783,541 B2 | 7/2014 | Shelton et al. | |
| 8,800,838 B2 | 8/2014 | Shelton | |
| 8,814,025 B2 | 8/2014 | Miller et al. | |
| 8,844,789 B2 | 9/2014 | Shelton et al. | |
| 8,899,464 B2 | 12/2014 | Hueil et al. | |
| 8,998,060 B2 | 4/2015 | Bruewer et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 2002/0165559 A1* | 11/2002 | Grant | A61B 17/07207 606/139 |
| 2005/0267325 A1* | 12/2005 | Bouchier | A61B 17/06004 600/37 |
| 2006/0135992 A1* | 6/2006 | Bettuchi | A61B 17/072 606/219 |
| 2007/0286892 A1* | 12/2007 | Herzberg | A61K 31/165 424/443 |
| 2008/0169328 A1 | 10/2008 | Schieb et al. | |
| 2011/0152924 A1* | 6/2011 | Gensini | A61L 15/28 606/213 |
| 2011/0278346 A1* | 11/2011 | Hull | A61B 17/00491 227/180.1 |
| 2011/0315742 A1* | 12/2011 | Olson | A61B 17/07207 227/177.1 |
| 2012/0080491 A1* | 4/2012 | Shelton, IV | A61B 17/00491 227/176.1 |
| 2012/0187179 A1* | 7/2012 | Gleiman | A61B 17/072 227/176.1 |
| 2012/0193392 A1* | 8/2012 | Krehel | A61B 17/068 227/175.1 |
| 2012/0199632 A1 | 8/2012 | Spivey et al. | |
| 2012/0241492 A1 | 9/2012 | Shelton et al. | |
| 2012/0241493 A1* | 9/2012 | Baxter, III | A61B 17/07292 227/175.1 |
| 2012/0241497 A1* | 9/2012 | Mandakolathur Vasudevan | A61B 17/00491 227/176.1 |
| 2012/0253298 A1* | 10/2012 | Henderson | A61B 17/00491 604/288.04 |
| 2012/0273547 A1* | 11/2012 | Hodgkinson | A61B 17/07207 227/176.1 |
| 2013/0037596 A1 | 2/2013 | Bear et al. | |
| 2013/0062391 A1* | 3/2013 | Boudreaux | A61B 17/00491 227/175.1 |
| 2013/0068816 A1 | 3/2013 | Vasudevan et al. | |
| 2013/0075446 A1 | 3/2013 | Wang et al. | |
| 2013/0075447 A1 | 3/2013 | Weisenburgh et al. | |
| 2013/0075450 A1* | 3/2013 | Schmid | A61B 17/00491 227/178.1 |
| 2013/0112731 A1* | 5/2013 | Hodgkinson | A61B 17/0682 227/176.1 |
| 2013/0164347 A1* | 6/2013 | Gensini | A61L 15/28 424/400 |
| 2013/0206813 A1 | 8/2013 | Nalagatla | |
| 2013/0256367 A1 | 10/2013 | Schieb et al. | |
| 2013/0256369 A1* | 10/2013 | Schmid | A61B 17/068 227/175.1 |
| 2013/0256373 A1* | 10/2013 | Schmid | A61B 17/07207 227/176.1 |
| 2013/0306707 A1* | 11/2013 | Viola | A61B 17/00491 227/179.1 |
| 2014/0209658 A1* | 7/2014 | Skalla | A61B 17/07292 227/175.1 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239042 A1 | 8/2014 | Simms et al. | |
| 2014/0239043 A1 | 8/2014 | Simms et al. | |
| 2014/0239044 A1 | 8/2014 | Hoffmann | |
| 2014/0246473 A1 | 9/2014 | Auld | |
| 2014/0263563 A1 | 9/2014 | Stokes et al. | |
| 2014/0367447 A1* | 12/2014 | Woodard, Jr. | A61B 17/072 227/176.1 |
| 2015/0238185 A1* | 8/2015 | Schellin | A61B 17/07207 227/175.1 |
| 2015/0238187 A1* | 8/2015 | Schellin | A61B 17/07207 227/180.1 |
| 2015/0272575 A1 | 10/2015 | Leimbach et al. | |
| 2015/0351754 A1 | 12/2015 | Harris et al. | |
| 2015/0351763 A1 | 12/2015 | Shelton et al. | |

OTHER PUBLICATIONS

Webster, R., et al. "PEGylated Proteins: Evaluation of Their Safety in the Absence of Definitive Metabolism Studies," *Drug Metabolism and Disposition*, vol. 35, No. 1, pp. 9-16 (2007).
U.S. Appl. No. 14/314,108, filed Jun. 25, 2014.
U.S. Appl. No. 14/314,125, filed Jun. 25, 2014.
U.S. Appl. No. 14/498,070 filed Sep. 26, 2014.
International Search Report and Written Opinion dated Jun. 1, 2016 for Application No. PCT/US2016/022747, 11 pgs.

* cited by examiner

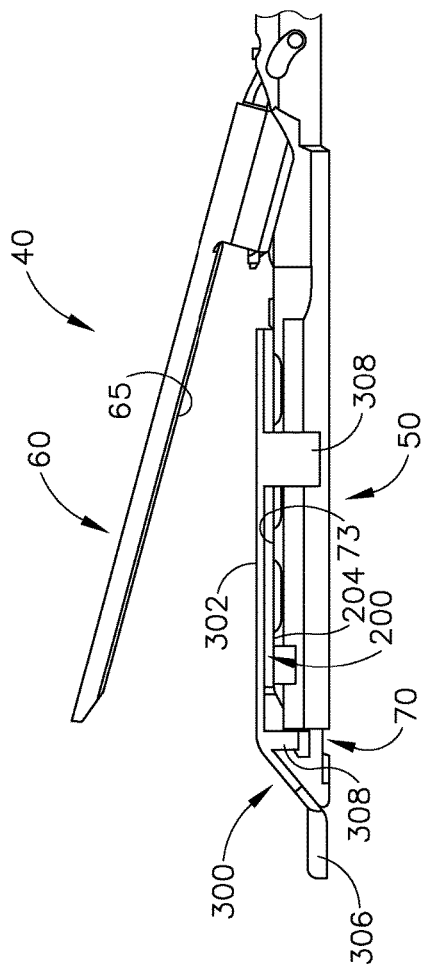
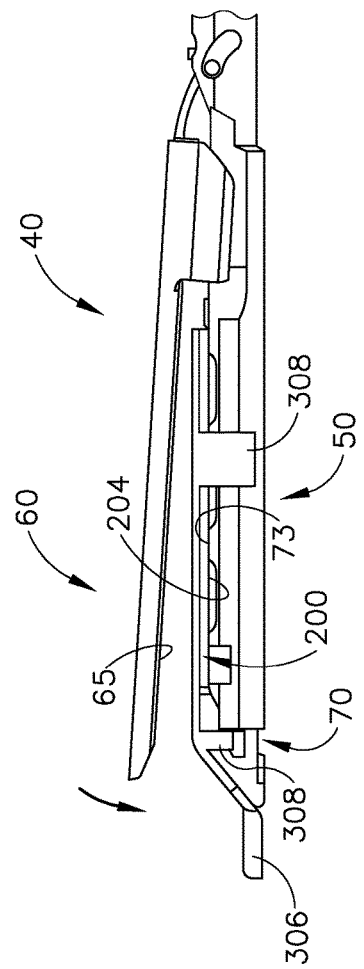
Fig.12B
Fig.12C

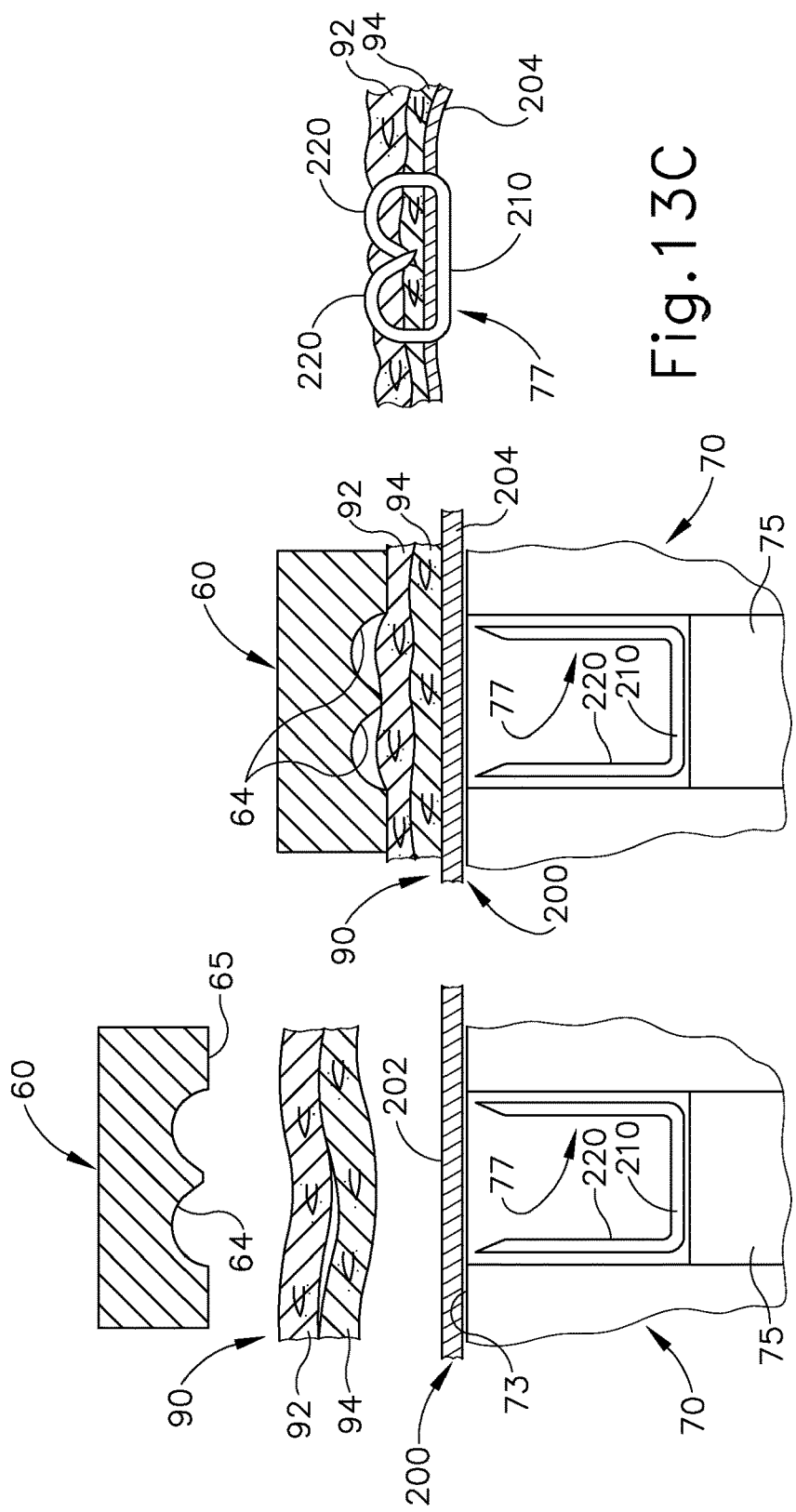

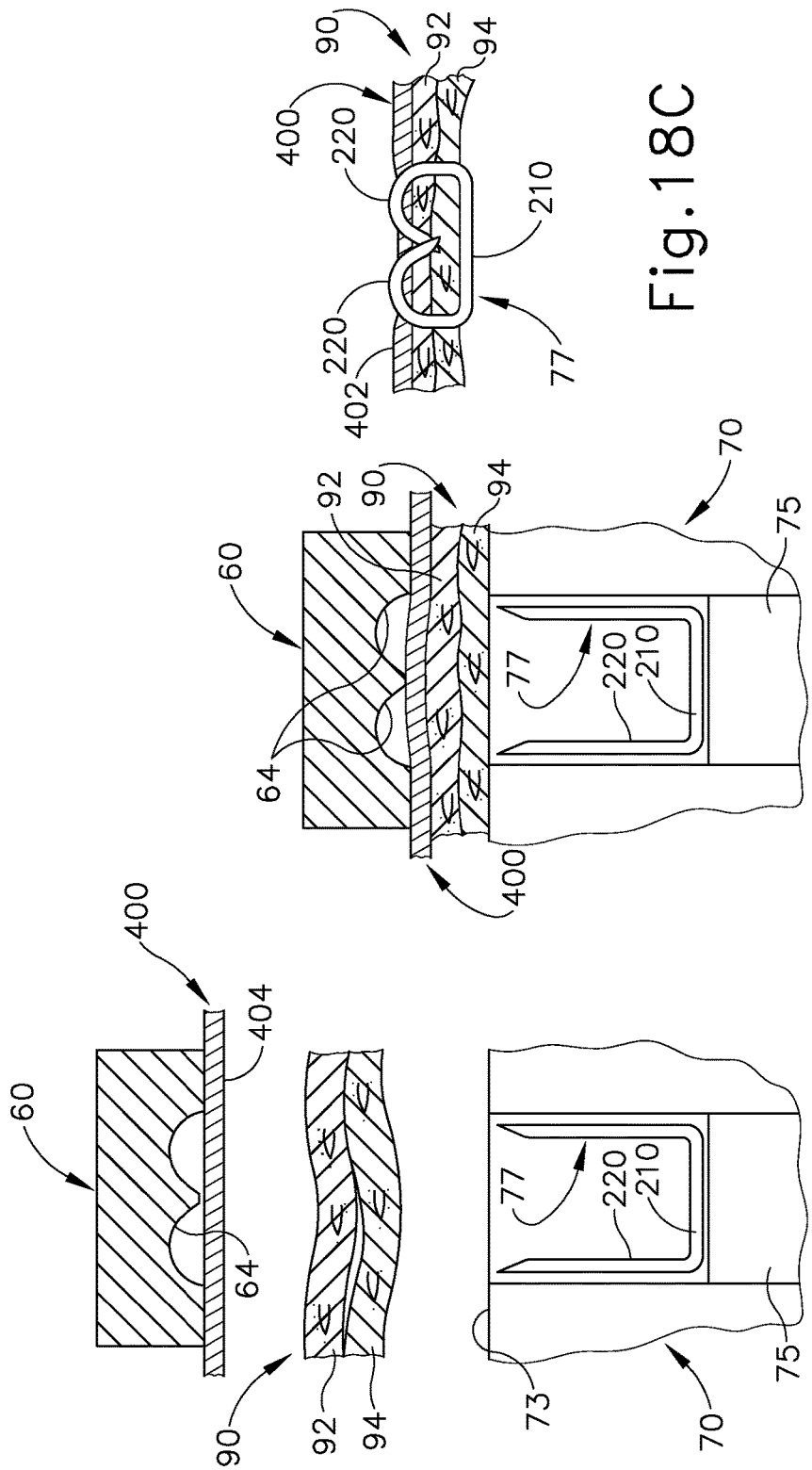

MALLEABLE BIOABSORBABLE POLYMER ADHESIVE FOR RELEASABLY ATTACHING A STAPLE BUTTRESS TO A SURGICAL STAPLER

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Pub. No. 2014/0243801, entitled "Surgical Instrument End Effector Articulation Drive with Pinion and Opposing Racks," published Aug. 28, 2014, and issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, now U.S. Pat. No. 9,717,497, issued Aug. 1, 2017; U.S. Patent Pub. No. 2014/0239042, entitled "Integrated Tissue Positioning and Jaw Alignment Features for Surgical Stapler," published Aug. 28, 2014, now U.S. Pat. No. 9,517,065; U.S. Patent Pub. No. 2014/0239036, entitled "Jaw Closure Feature for End Effector of Surgical Instrument," published Aug. 28, 2014, now U.S. Pat. No. 9,839,421, issued Dec. 12, 2017; U.S. Patent Pub. No. 2014/0239040, entitled "Surgical Instrument with Articulation Lock having a Detenting Binary Spring," published Aug. 28, 2014, now U.S. Pat. No. 9,867,615, issued Jan. 16, 2018; U.S. Patent Pub. No. 2014/0239043, entitled "Distal Tip Features for End Effector of Surgical Instrument," published Aug. 28, 2014, now U.S. Pat. No. 9,622,746, issued Apr. 18, 2017; U.S. Patent Pub. No. 2014/0239037, entitled "Staple Forming Features for Surgical Stapling Instrument," published Aug. 28, 2014, now U.S. Pat. No. 10,092,292, issued Oct. 9, 2018; U.S. Patent Pub. No. 2014/0239038, entitled "Surgical Instrument with Multi-Diameter Shaft," published Aug. 28, 2014, now U.S. Pat. No. 9,795,379, issued Oct. 24, 2017; and U.S. Patent Pub. No. 2014/0239044, entitled "Installation Features for Surgical Instrument End Effector Cartridge," published Aug. 28, 2014, now U.S. Pat. No. 9,808,248, issued Nov. 7, 2017. The disclosure of each of the above-cited U.S. Patent Publications is incorporated by reference herein.

Additional surgical stapling instruments are disclosed in U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, now U.S. Pat. No. 9,597,082, issued Mar. 21, 2017; U.S. Pub. No.

2014/0246473, entitled "Rotary Powered Surgical Instruments with Multiple Degrees of Freedom," published Sep. 4, 2014, now U.S. Pat. No. 9,398,911, issued Jul. 26, 2016; U.S. Pub. No. 2013/0206813, entitled "Linear Stapler," published Aug. 15, 2013; U.S. Pub. No. 2008/0169328, entitled "Buttress Material for Use with a Surgical Stapler," published Jul. 17, 2008; U.S. patent application Ser. No. 14/300,804, entitled "Woven and Fibrous Materials for Reinforcing a Staple Line," filed Jun. 10, 2014, and published as U.S. Pat. Pub. No. 2015/0351754 on Dec. 10, 2015, now U.S. Pat. No. 9,848,871, issued Dec. 26, 2017; U.S. patent application Ser. No. 14/300,811, entitled "Devices and Methods for Sealing Staples in Tissue", published as U.S. Pat. Pub. No. 2015/0351763 on Dec. 10, 2015, now U.S. Pat. No. 9,936,954, issued Apr. 10, 2018; and U.S. patent application Ser. No. 14/498,070, entitled "Radically Expandable Staple Line" filed Sep. 26, 2014, now U.S. Patent Pub. No. 2016/0089146, published Mar. 31, 2016. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 12B depicts a side elevational view of the buttress and retainer of FIG. 10 engaging the end effector of FIG. 3, with the anvil of the end effector in an open position;

FIG. 12C depicts a side elevational view of the buttress and retainer of FIG. 10 engaging the end effector of FIG. 3, with the anvil of the end effector moving toward a closed position;

FIG. 13A depicts a cross-sectional view of a portion of the end effector and buttress assembly of FIG. 12D, with tissue positioned between the buttress and the anvil, and with the anvil in an open position;

FIG. 13B depicts a cross-sectional view of a portion of the end effector and buttress assembly of FIG. 12D, with tissue positioned between the buttress and the anvil, and with the anvil in a closed position;

FIG. 13C depicts a cross-sectional view of a staple and the buttress of FIG. 12D being secured to tissue by the end effector of FIG. 12D;

FIG. 18A depicts a cross-sectional view of a portion of the end effector and buttress assembly of FIG. 17B, with tissue positioned between the buttress and the staple cartridge, and with the anvil in an open position;

FIG. 18B depicts a cross-sectional view of a portion of the end effector and buttress assembly of FIG. 17B, with tissue positioned between the buttress and the staple cartridge, and with the anvil in a closed position;

FIG. 18C depicts a cross-sectional view of a staple and the buttress of FIG. 17B being secured to tissue by the end effector of FIG. 17B;

Figure 1:
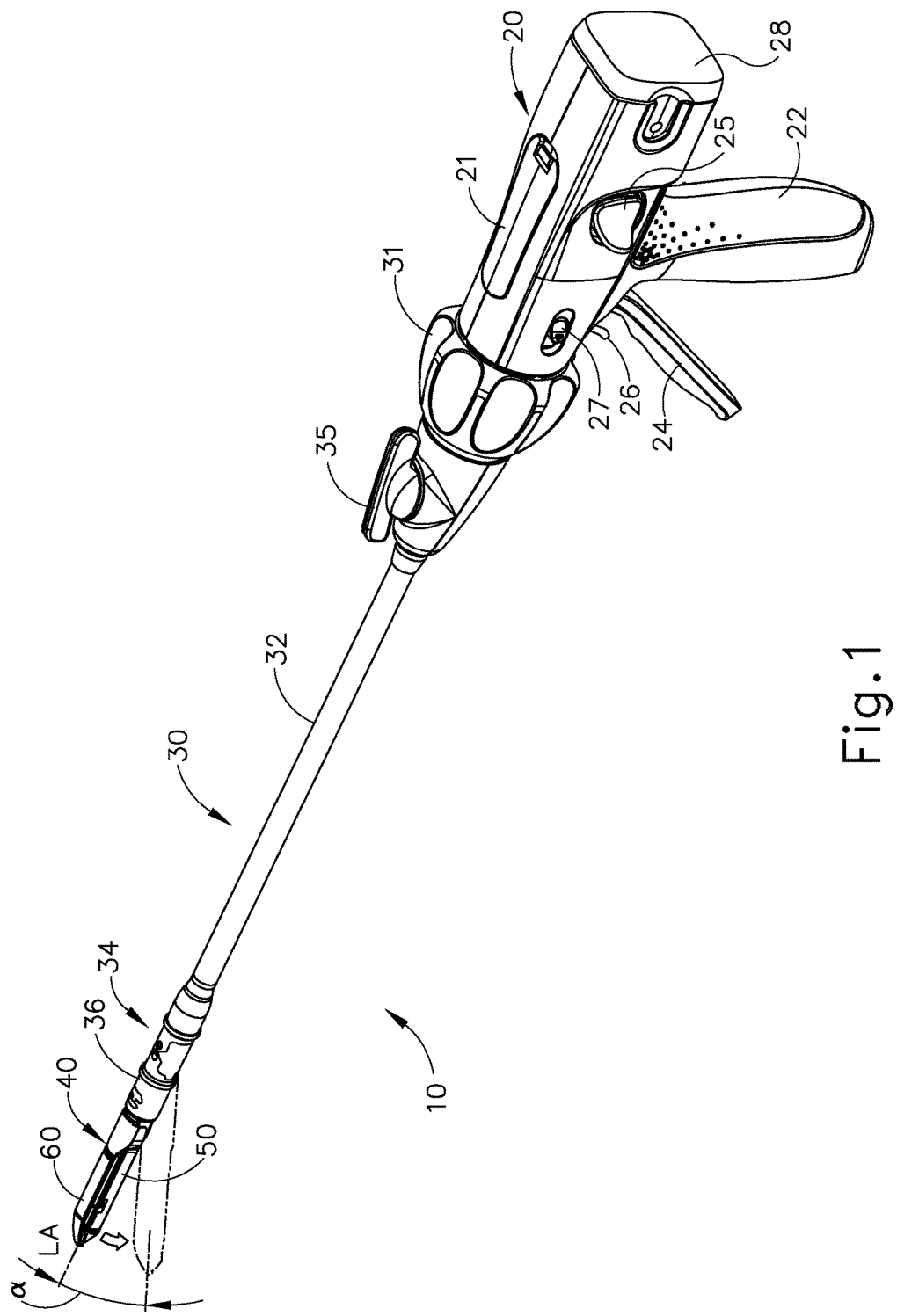
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
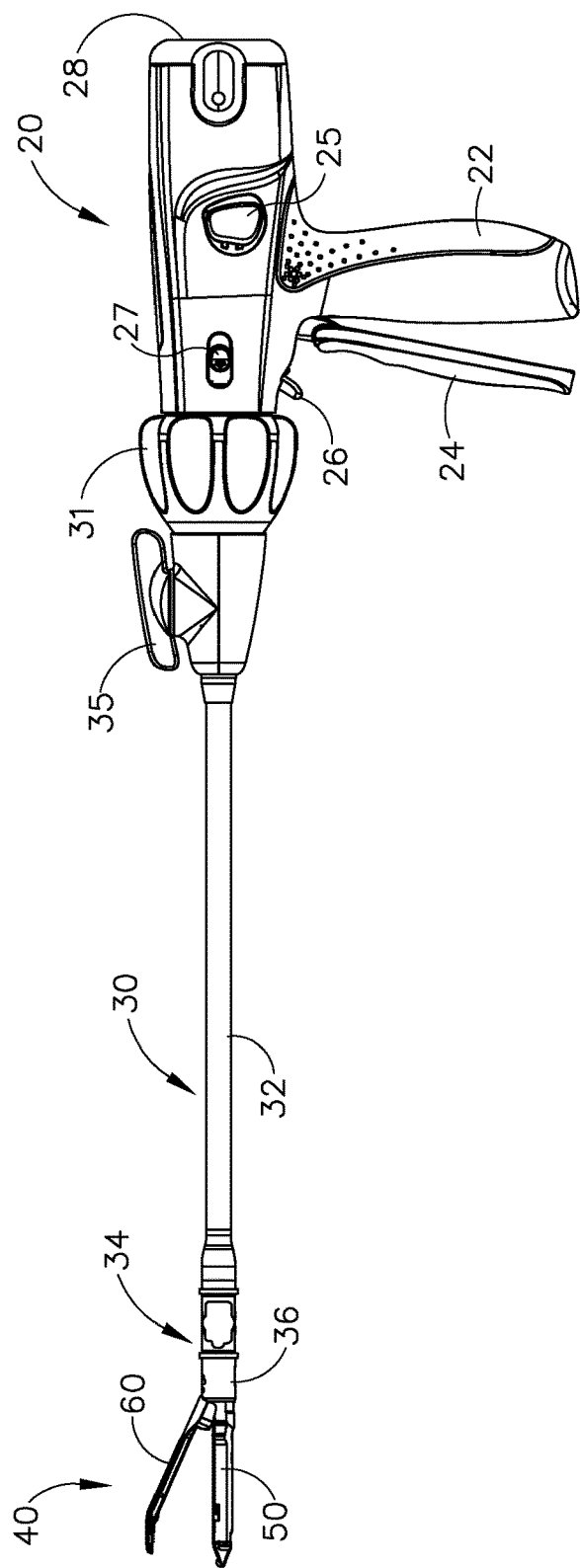
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
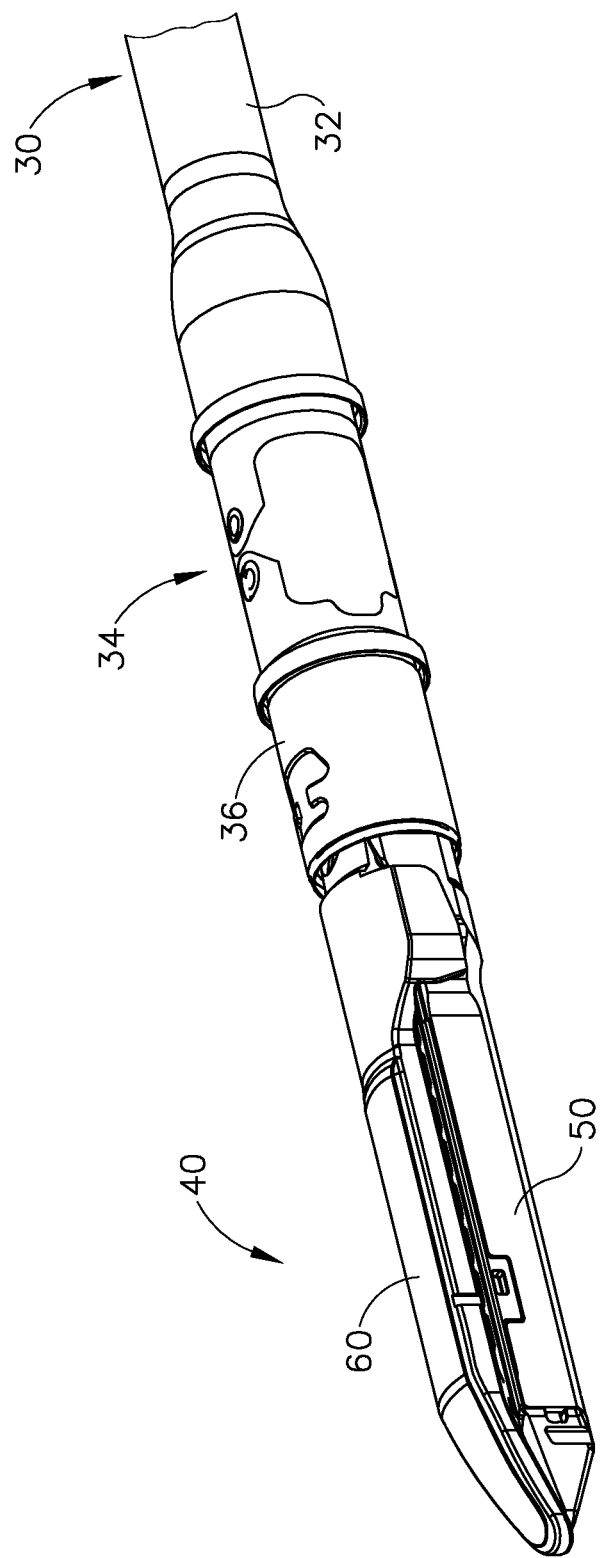
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein. Articulation section (34) may also be constructed and operable in accordance with at least some of the teachings of U.S. patent application Ser. No. 14/314,125, entitled "Articulation Drive Features for Surgical Stapler," filed Jun. 25, 2014, now U.S. Patent Pub. No. 2015/0374360, publishes Dec. 31, 2105, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, now U.S. Pat. No. 9,795,379, issued Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that lower jaw (50) may take will be apparent to those of ordinary skill in the art in view of the teachings herein.

Figure 4:
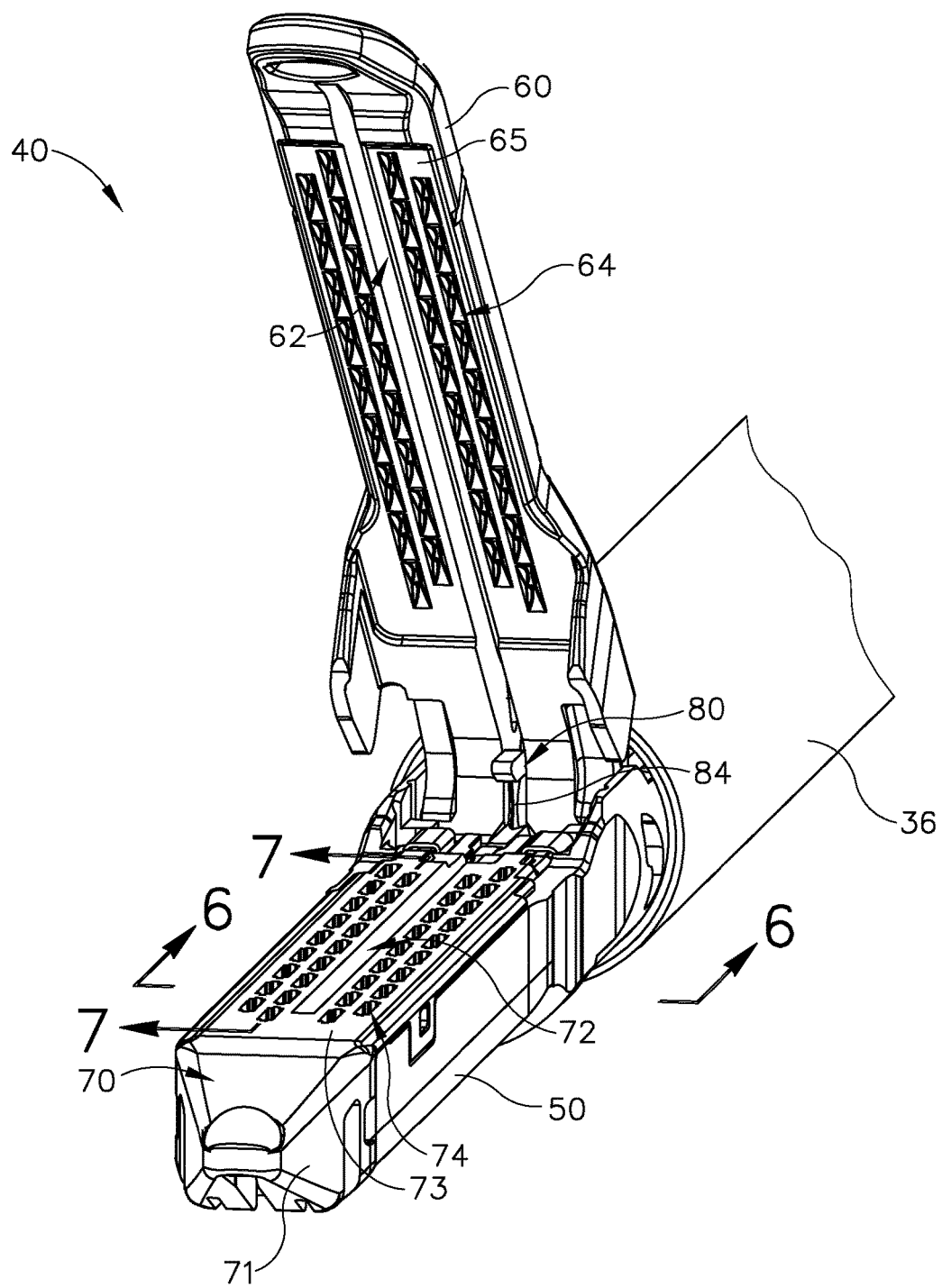
FIG. 4 depicts a perspective view of the end effector of FIG. 3, with the end effector in an open configuration.
Figure 5:
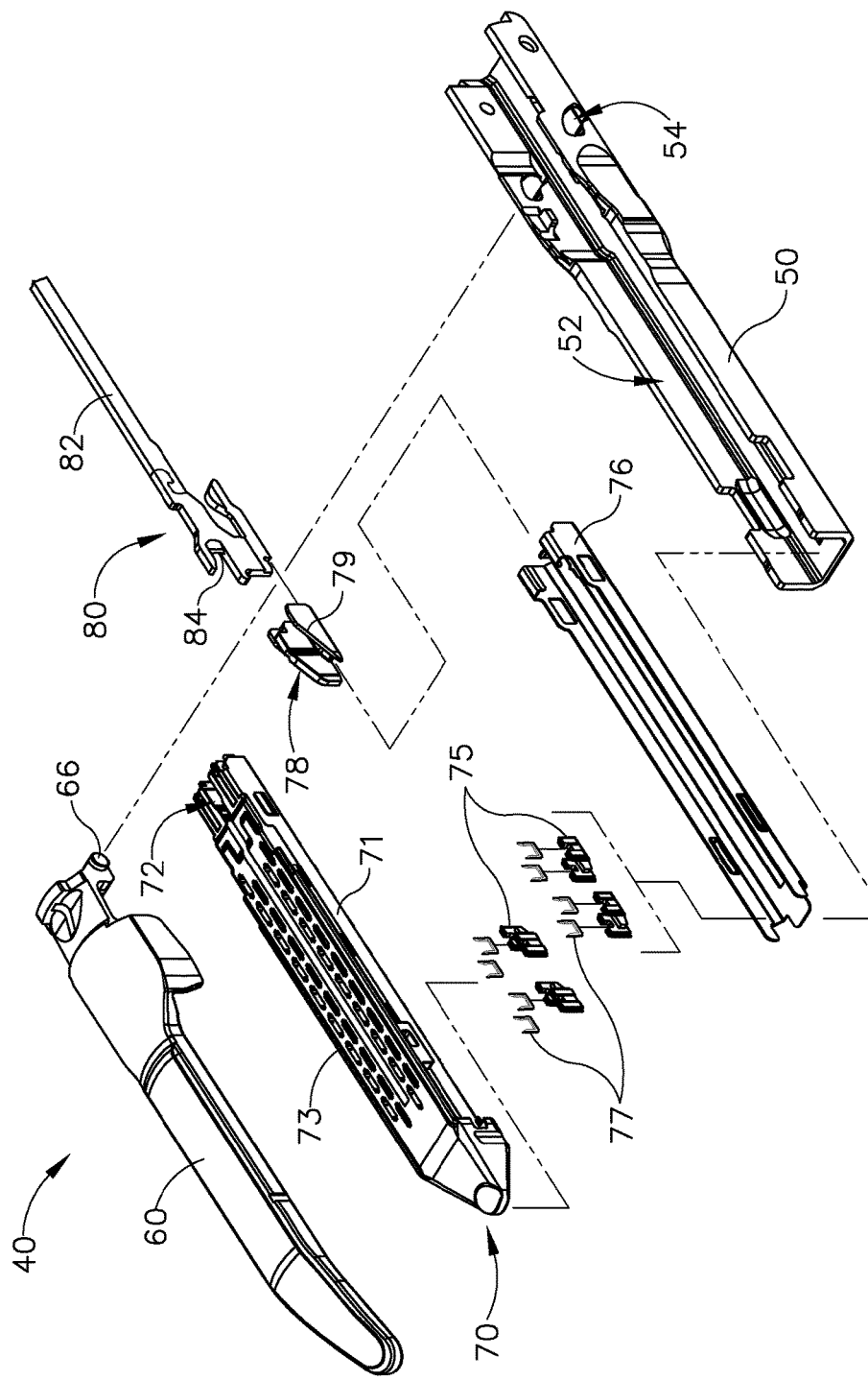
FIG. 5 depicts an exploded perspective view of the end effector of FIG. 3.
Figure 6:
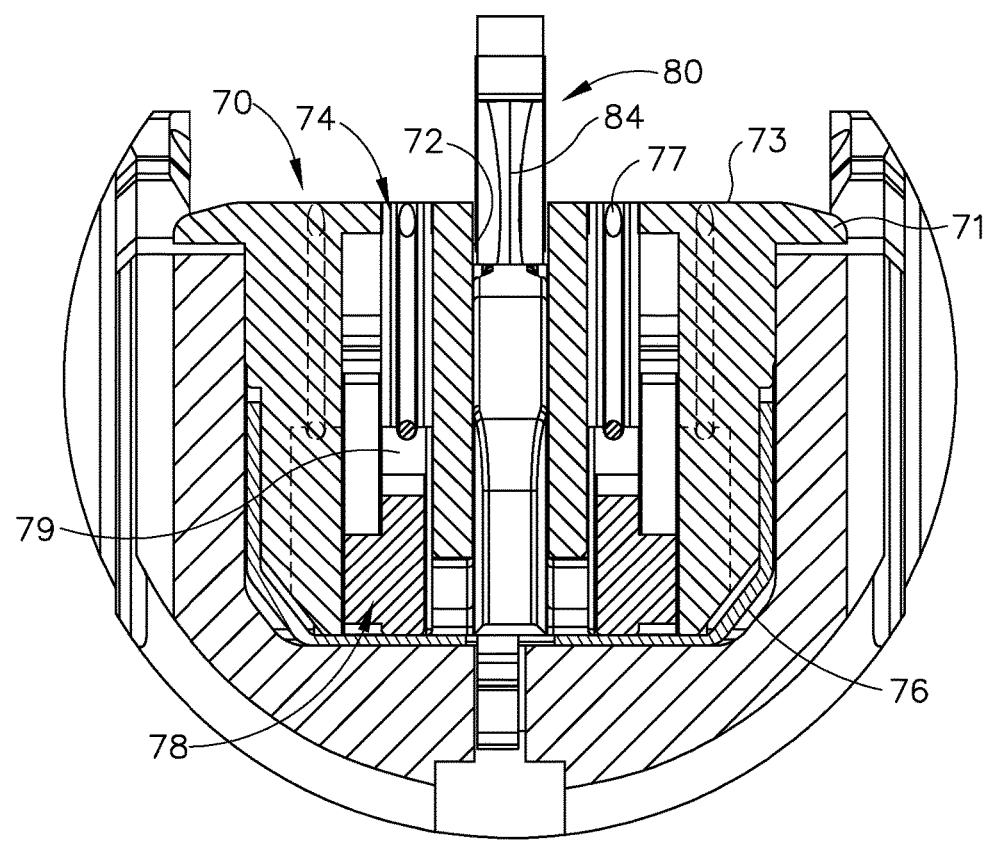
FIG. 6 depicts a cross-sectional end view of the end effector of FIG. 3, taken along line 6-6 of FIG. 4.
Figure 7A:
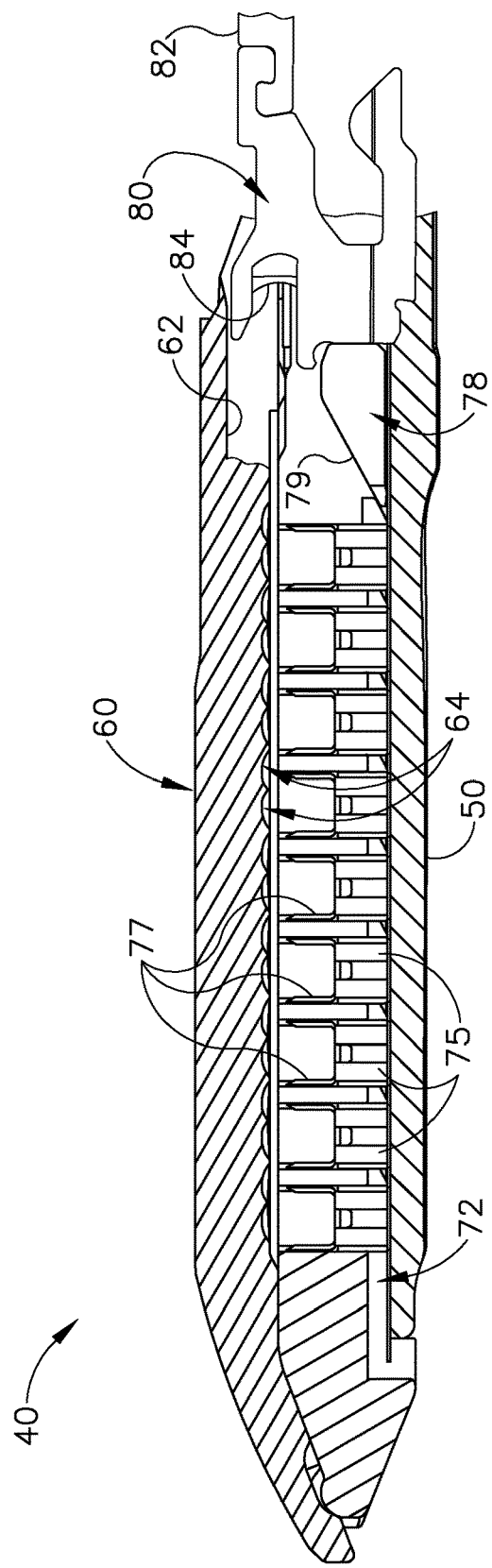
FIG. 7A depicts a cross-sectional side view of the end effector of FIG. 3, taken along line 7-7 of FIG. 4, with a firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64) that are formed in the underside (65) of anvil (60). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U.S. patent application Ser. No. 13/780,106, entitled "Integrated Tissue Positioning and Jaw Alignment Features for Surgical Stapler," filed Feb. 28, 2013, published as U.S. Pub. No. 2014/0239042 on Aug. 28, 2014, now U.S. Pat. No. 9,517,065, issued Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; at least some of the teachings of U.S. Pub. No. 2014/0239036, entitled "Jaw Closure Feature for End Effector of Surgical Instrument," published Aug. 28, 2014; now U.S. Pat. No. 9,839,421, issued Dec. 12, 2017; and/or at least some of the teachings of U.S. Pub. No. 2014/0239037, entitled "Staple Forming Features for Surgical Stapling Instrument," published Aug. 28, 2014, now U.S. Pat. No. 10,092,292, issued Oct. 9, 2018, the disclosure of which is incorporated by reference herein. Other suitable forms that anvil (60) may take will be apparent to those of ordinary skill in the art in view of the teachings herein.

Figure 7B:
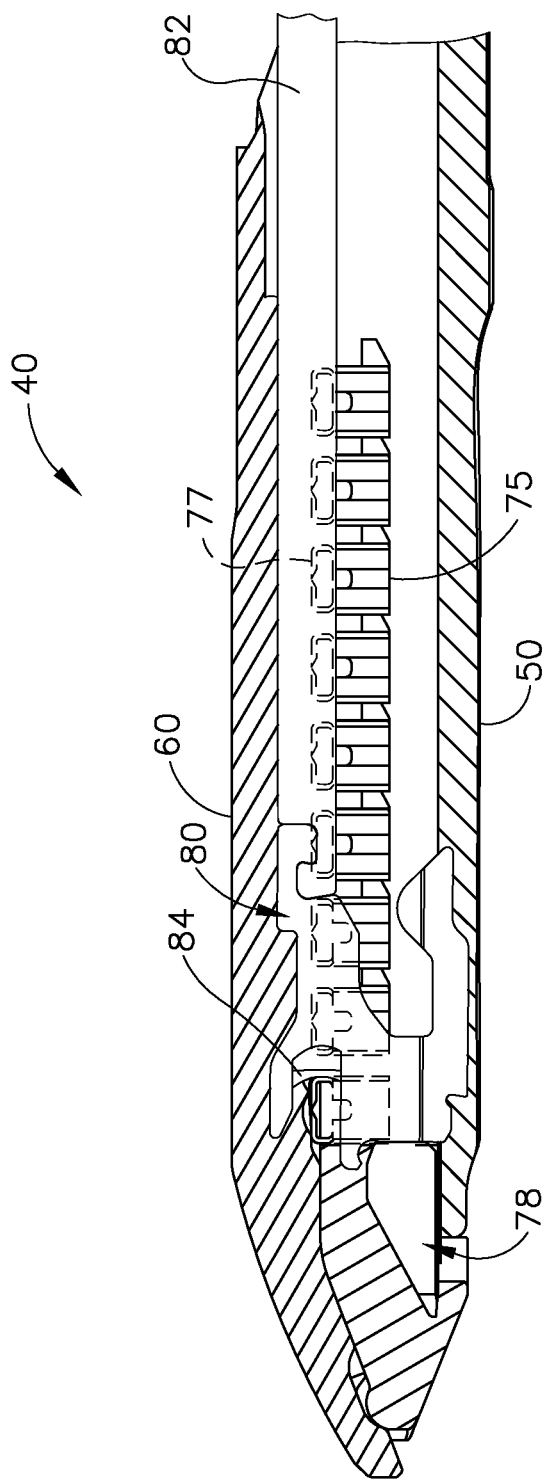
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. Pub. No. 2014/0239041, entitled "Lockout Feature for Movable Cutting Member of Surgical Instrument," published Aug. 28, 2014, now U.S. Pat. No. 9,717,497, issued Aug. 1, 2017, the disclosure of which is incorporated by reference herein; and/or at least some of the teachings of U.S. patent application Ser. No. 14/314,108, entitled "Method of Using Lockout Features for Surgical Stapler Cartridge," filed on Jun. 25, 2014, now U.S. Patent Pub. No. 2015/0374373, published Dec. 31, 2015, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, now U.S. Pat. No. 9,839,421, issued Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, now U.S. Patent Pub. No. 2015/0374373, published Dec. 31, 2015, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

In the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). In some such versions, firing beam (82) may only be advanced distally when anvil

(60) is in a fully closed position relative to lower jaw (50). After firing beam (82) is advanced distally to sever tissue and drive staples (77) as described above with reference to FIGS. 7A-7B, the drive assembly for firing beam (82) may be automatically reversed to drive firing beam (82) proximally back to the retracted position (e.g., back from the position shown in FIG. 7B to the position shown in FIG. 7A). Alternatively, the operator may actuate firing beam reverse switch (27), which may reverse the drive assembly for firing beam (82) in order to retract firing beam (82) to a proximal position. Handle assembly (20) of the present example further includes a bailout feature (21), which is operable to provide a mechanical bailout allowing the operator to manually retract firing beam (82) proximally (e.g., in the event of power loss while firing beam (82) is in a distal position, etc.).

By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein. As another merely illustrative example, the features that are operable to provide motorized actuation of firing beam (82) may be configured and operable in accordance with at least some of the teachings of U.S. Pat. No. 8,453,914, entitled "Motor-Driven Surgical Cutting Instrument with Electric Actuator Directional Control Assembly," issued Jun. 4, 2013, the disclosure of which is incorporated by reference herein. As yet another merely illustrative example, the features that are operable to provide motorized actuation of firing beam (82) may be configured and operable in accordance with at least some of the teachings of U.S. patent application Ser. No. 14/226,142, entitled "Surgical Instrument Comprising a Sensor System," filed Mar. 26, 2014, published as U.S. Pat. Pub. No. 2015/0272575 on Oct. 1, 2015, now U.S. Pat. No. 9,313,642, issued Mar. 13, 2018, the disclosure of which is incorporated by reference herein.

Other suitable components, features, and configurations that may be used to provide motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be manually actuated in accordance with at least some of the teachings of any other reference cited herein.

Figure 8:
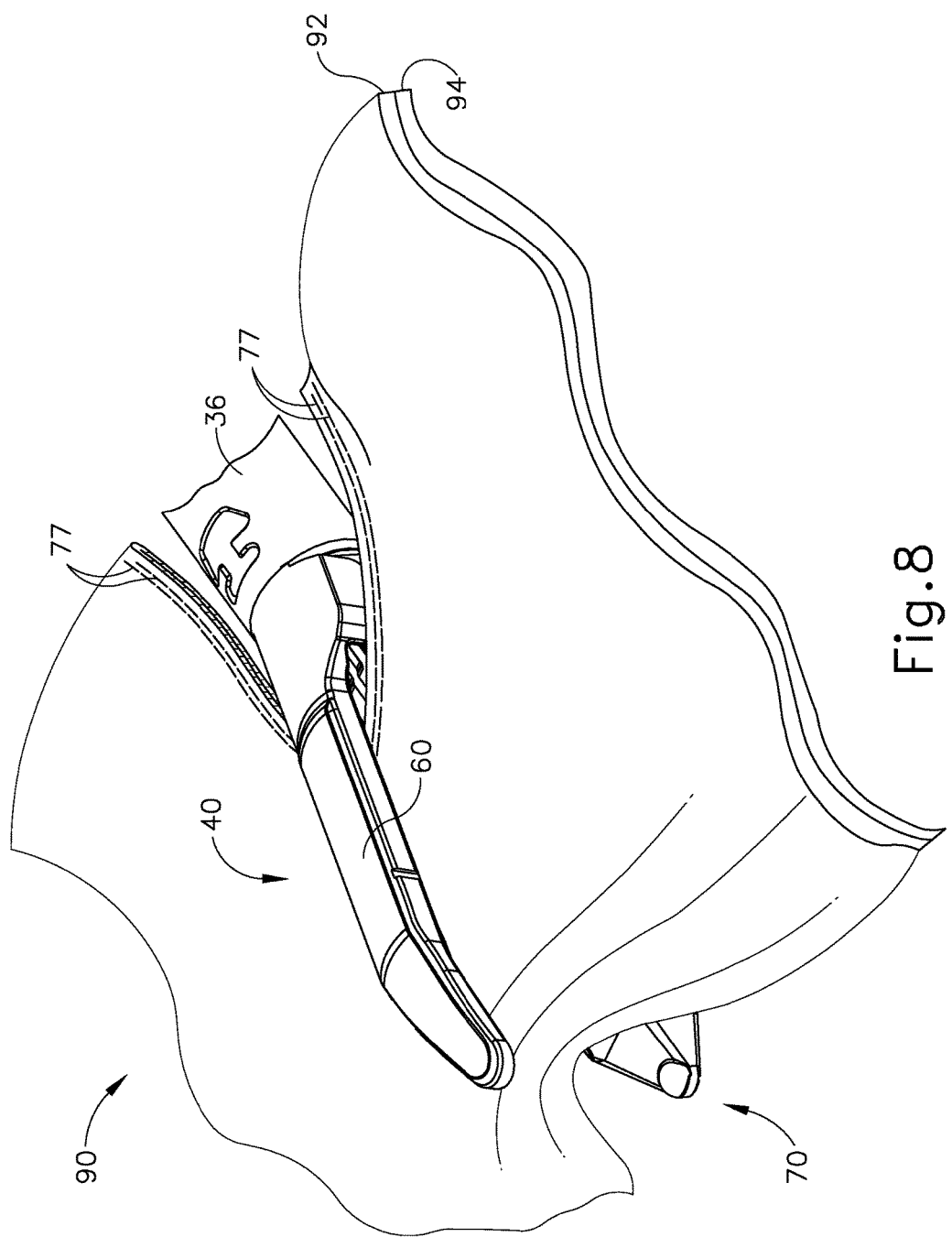
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress for Surgical Stapler

As noted above, it may be desirable in some instances to equip end effector (40) with a buttress material to reinforce the mechanical fastening of tissue (90) provided by staples (77). Such a buttress may prevent the applied staples (77) from pulling through tissue (90) and may otherwise reduce a risk of tissue (90) tearing at or near the site of applied staples (77). In addition to or as an alternative to providing structural support and integrity to a line of staples (77), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress for Surgical Stapler

Figure 9:
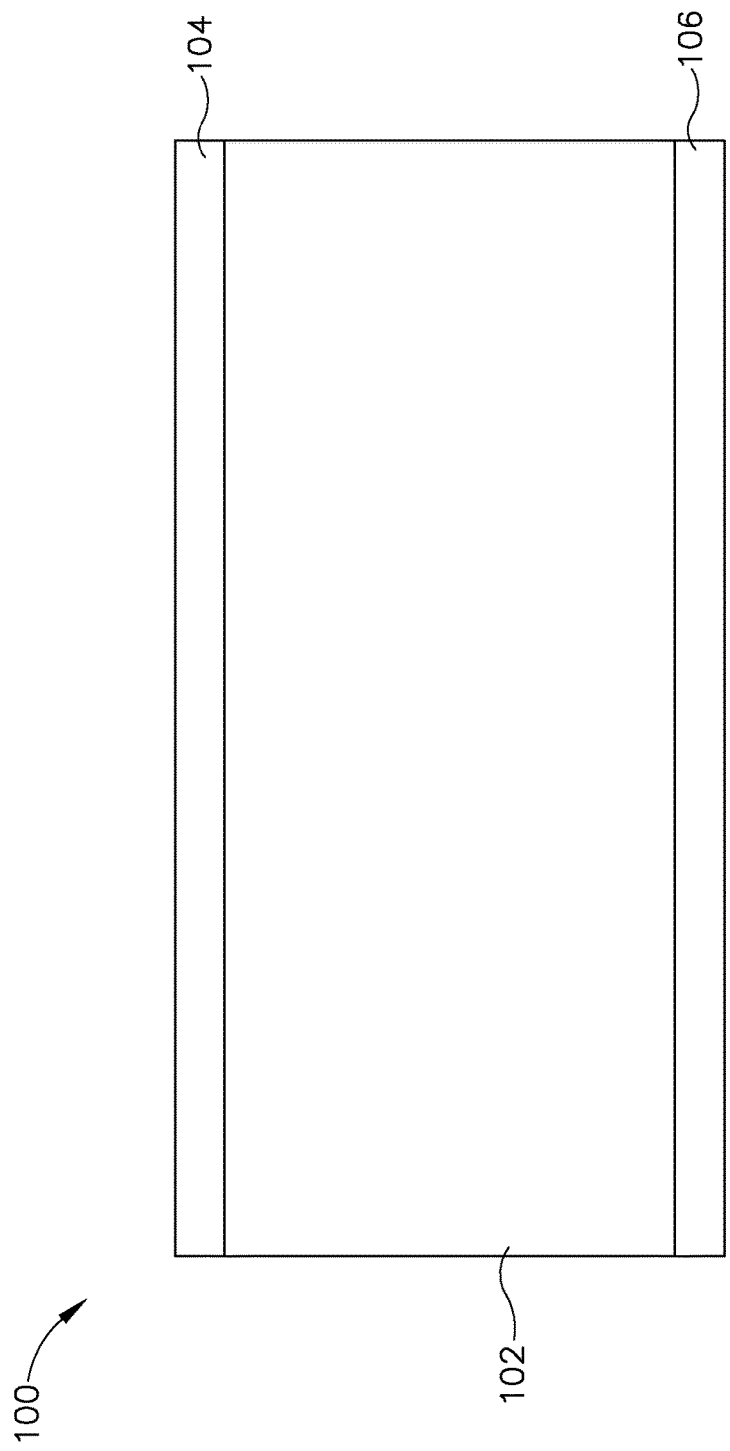
FIG. 9 depicts a cross-sectional view of an exemplary buttress assembly that may be used with the end effector of FIG. 3.
Figure 10:
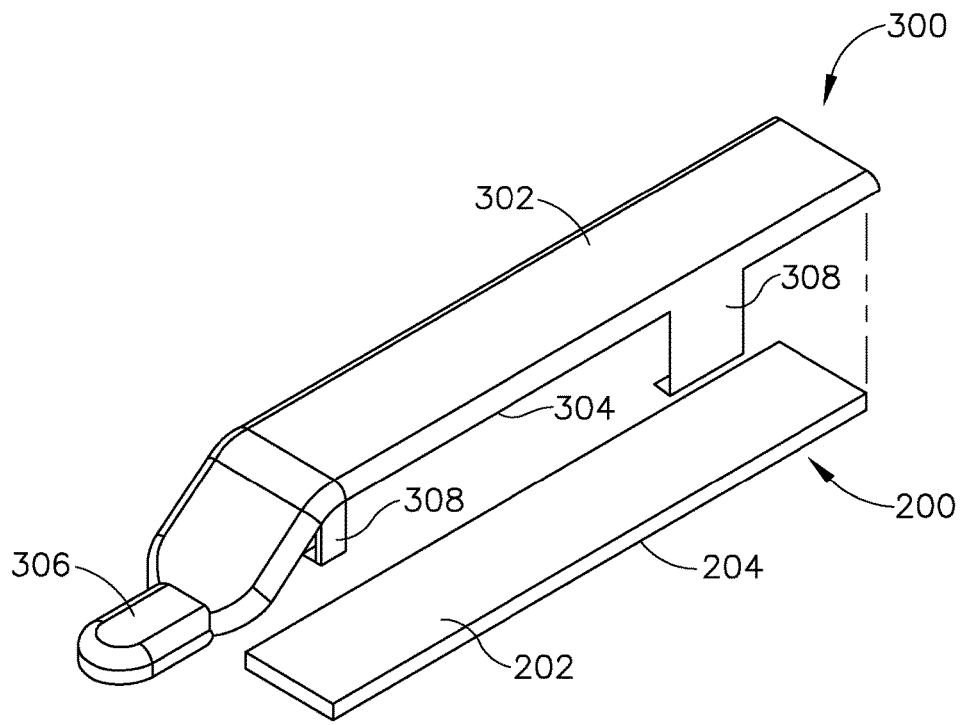
FIG. 10 depicts an exploded perspective view of an exemplary buttress and retainer.
Figure 11:
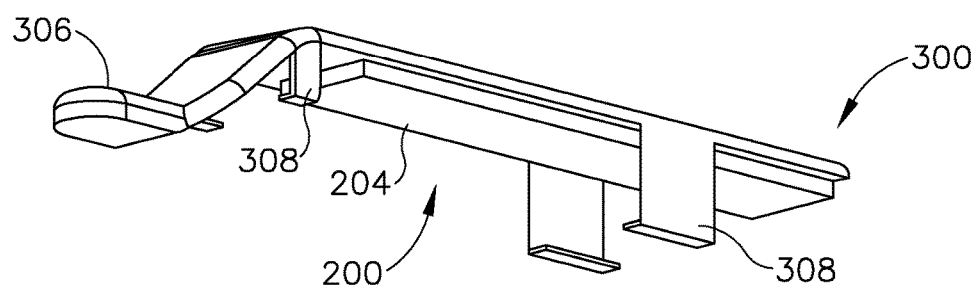
FIG. 11 depicts a perspective view of the buttress and retainer of FIG. 10, with the buttress secured to the underside of the retainer.

FIG. 9 shows an exemplary buttress assembly (100) with a basic composition. Buttress assembly (100) of this example comprises a buttress body (102), an upper adhesive layer (104), and a lower adhesive layer (106). In the present example, buttress body (102) comprises a strong yet flexible material configured to structurally support a line of staples (77). In addition or in the alternative, buttress body (102) may comprise a material including, for example, a hemostatic agent such as fibrin to assist in coagulating blood and reduce bleeding at the severed and/or stapled surgical site along tissue (90).

As another merely illustrative example, buttress body (102) may comprise other adjuncts or hemostatic agents such as thrombin may be used such that buttress body (102) may assist to coagulate blood and reduce the amount of bleeding at the surgical site. The hemostatic abilities of such adjuncts may also contribute to the use of such adjuncts as adhesives and sealants. The agents may assist to coagulate blood at a surgical site, which allows tissue surrounding such blood to stick together and may prevent leaks along the stapled tissue site, for example. Other adjuncts or reagents that may be incorporated into buttress body (102) may further include but are not limited to medical fluid or matrix components. By way of example only, buttress body (102) may include natural or genetically engineered absorbable polymers or synthetic absorbable polymers, or mixtures thereof. Merely illustrative examples of natural or genetically engineered absorbable polymers are proteins, polysaccharides and combinations thereof. Merely illustrative examples of proteins that may be used include prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of synthetic absorbable polymers are aliphatic polyester polymers, copolymers, and/or combinations thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one). Other suitable compounds, materials, substances, etc., that may be used in a medical fluid or matrix will be apparent to those of ordinary skill in the art in view of the teachings herein.

Buttress body (102) may alternatively comprise a fibrous pad, a foam, a mesh, a weave, and/or another structure capable of containing an adhesive and/or other type of medical fluid. In addition or in the alternative, buttress body (102) may simply comprise a mesh, a weave, and/or some other structure that is constructed to provide structural support or integrity to a line of staples (77) applied through tissue (90). Such a material and structure may be relatively thin and in some instances may be substantially non-compressible. By way of further example only, buttress body (102) may be constructed in accordance with at least some of the teachings of U.S. Patent Pub. No. 2012/0241493, entitled "Tissue Thickness Compensator Comprising Controlled Release and Expansion," published Sep. 27, 2012, the disclosure of which is incorporated by reference herein; U.S. Patent Pub. No. 2013/0068816, entitled "Surgical Instrument and Buttress Material," published Mar. 21, 2013, the disclosure of which is incorporated by reference herein; U.S. Patent Pub. No. 2013/0062391, entitled "Surgical Instrument with Fluid Fillable Buttress," published Mar. 14, 2013, now U.S. Pat. No. 9,999,408, issued Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, now U.S. Pat. No. 9,942,170, issued Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, now U.S. Pat. No. 9,393,018, issued Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, the disclosure of which is incorporated by reference herein; and/or U.S. Patent Pub. No. 2013/0256367, entitled "Tissue Thickness Compensator Comprising a Plurality of Medicaments," published Oct. 3, 2013, now U.S. Pat. No. 9,211,120, issued Dec. 15, 2015, the disclosure of which is incorporated by reference herein.

In the present example, buttress body (102) comprises a woven mesh of VICRYL® (polyglactin 910) material by Ethicon US, LLC. VICRYL® woven mesh is prepared from a synthetic absorbable copolymer of glycolide and lactide, derived respectively from glycolic and lactic acids. This tightly woven mesh is prepared from uncoated, undyed fiber identical in composition to that used in VICRYL® synthetic absorbable suture, which has been found to be inert, nonantigenic, nonpyrogenic, and to elicit only a mild tissue reaction during absorption. VICRYL® woven mesh is intended for use as a buttress to provide temporary support during the healing process. Alternatively, any other suitable materials or combinations of materials may be used in addition to or as an alternative to VICRYL® material to form buttress body (102).

In versions where buttress body (102) is formed as a mesh, it should be understood that various kinds of mesh geometry may be used. By way of example only, buttress body (102) may be formed as a woven mesh, a knitted mesh, or a warp knitted mesh. Regardless of whether buttress body (102) is formed as a mesh or not, buttress body (102) is porous in some examples. As described in greater detail below, an adhesive layer (104, 106) may be provided on buttress body (102) in order to adhere buttress body (102) to underside (65) of anvil (60) or deck (73) of staple cartridge (70). In some versions where buttress body (102) is porous, the material forming adhesive layer (104, 106) may pass through buttress body (102) to reach the outer surface of buttress body (102) that is opposite to the surface on which adhesive layer (104, 106) is disposed.

By way of example only, upper adhesive layer (104) may be used to secure buttress assembly (100) to the underside (304) of a retainer (300) as will be described in greater detail below; while lower adhesive layer (106) is used to secure buttress assembly (100) to deck (73) of staple cartridge (70). In some versions of this example, lower adhesive layer (106) is configured to provide stronger adherence than upper adhesive layer (104). In some illustrative variations of this example, one or more features of retainer (300) (e.g., flanges, clips, etc.) are configured to selectively retain buttress assembly (100) against underside (304) of retainer (300), such that upper adhesive layer (104) is omitted; while lower adhesive layer (106) is used to secure buttress assembly (100) to deck (73) of staple cartridge (70). In addition or in the alternative, an adhesive material may be applied to the lower surface of a porous version of buttress body (102) to form lower adhesive layer (106), and some of that adhesive material may pass through buttress body (102) to form upper adhesive layer (104). In some such versions, lower adhesive layer (106) ultimately has more adhesive material than upper adhesive layer (104), such that lower adhesive layer (106) provides greater adhesion than upper adhesive layer (104).

In yet another merely illustrative example, lower adhesive layer (106) may be used to secure buttress assembly (100) to the upper side (302) of a retainer (300) as will be described in greater detail below; while upper adhesive layer (104) is used to secure buttress assembly to underside (65) of anvil (60) of end effector (40). In some versions of this example, upper adhesive layer (104) is configured to provide stronger adherence than lower adhesive layer (106). In some illustrative variations of this example, one or more features of retainer (300) (e.g., flanges, clips, etc.) are configured to selectively retain buttress assembly (100) against upper side (302) of retainer (300), such that lower adhesive layer (106) is omitted; while upper adhesive layer (104) is used to secure buttress assembly (100) to underside (65) of anvil (60). In addition or in the alternative, an adhesive material may be applied to the upper surface of a porous version of buttress body (102) to form upper adhesive layer (104), and some of that adhesive material may pass through buttress body (102) to form lower adhesive layer (106). In some such versions, upper adhesive layer (104) ultimately has more adhesive material than lower adhesive layer (106), such that upper adhesive layer (104) provides greater adhesion than lower adhesive layer (106).

Various suitable compositions that may be used to form each adhesive layer (104, 106), as well as various forms that each adhesive layer (104, 106) may take, will be described in greater detail below.

It should also be understood that buttress assembly (100) may include an impermeable layer or a semi impermeable layer interposed between buttress body (102) and adhesive layer (102), to prevent or restrict migration of adhesive material from adhesive layer (104, 106) into buttress body (100). By way of example only, body (102) may be formed of a porous media (e.g., ETHISORB™ by Codman of Raynham, Mass.); while the semi impermeable layer may comprise polydioxanone (PDS). In versions where buttress assembly (100) comprises an impermeable layer or a semi impermeable layer to prevent or restrict migration of adhesive material from adhesive layer (104, 106) into buttress body (100), such a layer may be integrated into buttress body (102) such that the layer permits the adhesive to migrate at least partially into buttress body (102) but not across the full thickness of buttress body (102). Various suitable ways in which an impermeable layer or a semi impermeable layer may be integrated into buttress assembly (100) to prevent or restrict migration of an adhesive material will be apparent to those of ordinary skill in the art in view of the teachings herein.

B. Exemplary Instrument and Technique for Securing Buttress to Deck of Staple Cartridge FIGS. 10-12D show a combination of an exemplary buttress (200) with an exemplary retainer (300). Buttress (200) of this example may be constructed in accordance with the teachings above relating to buttress assembly (100) and/or in accordance with other teachings herein. Buttress (200) includes an upper side (202) and an underside (204). In the present example, underside (204) includes an adhesive (e.g., like lower adhesive layer (106)) to secure buttress (200) to deck (73) of staple cartridge (70) as described in greater detail below.

Retainer (300) of this example comprises an upper side (302), an underside (304), a distally projecting tongue (306), and a set of resilient latches (308). Upper side (302) and underside (304) are each generally flat in the present example, though it should be understood that upper side (302) and/or underside (304) may include various kinds of features as described elsewhere herein. Tongue (306) is configured to provide a grip for an operator, thereby facilitating grasping and handling of retainer (300) during use. Latches (308) are configured to releasably secure retainer (300) to lower jaw (50) of end effector (40) as will be described in greater detail below. By way of example only, retainer (300) may be formed of molded plastic. Alternatively, retainer (300) may be formed using any other suitable material(s) or technique(s).

In the present example, buttress (200) is secured to underside (304) of retainer (300), such that upper side (202) of buttress (200) apposes underside (304) of retainer (300). In some versions, an adhesive such as upper adhesive layer (104) provides releasable adhesion of buttress (200) to underside (304) of retainer (300). In some other versions, retainer (300) includes one or more features (e.g., flanges, clips, etc.) that are configured to selectively retain buttress (200) against underside (304) of retainer (300). Various suitable ways in which buttress (200) may be releasably secured to underside (304) of retainer (300) will be apparent to those of ordinary skill in the art in view of the teachings herein.

Figure 12A:
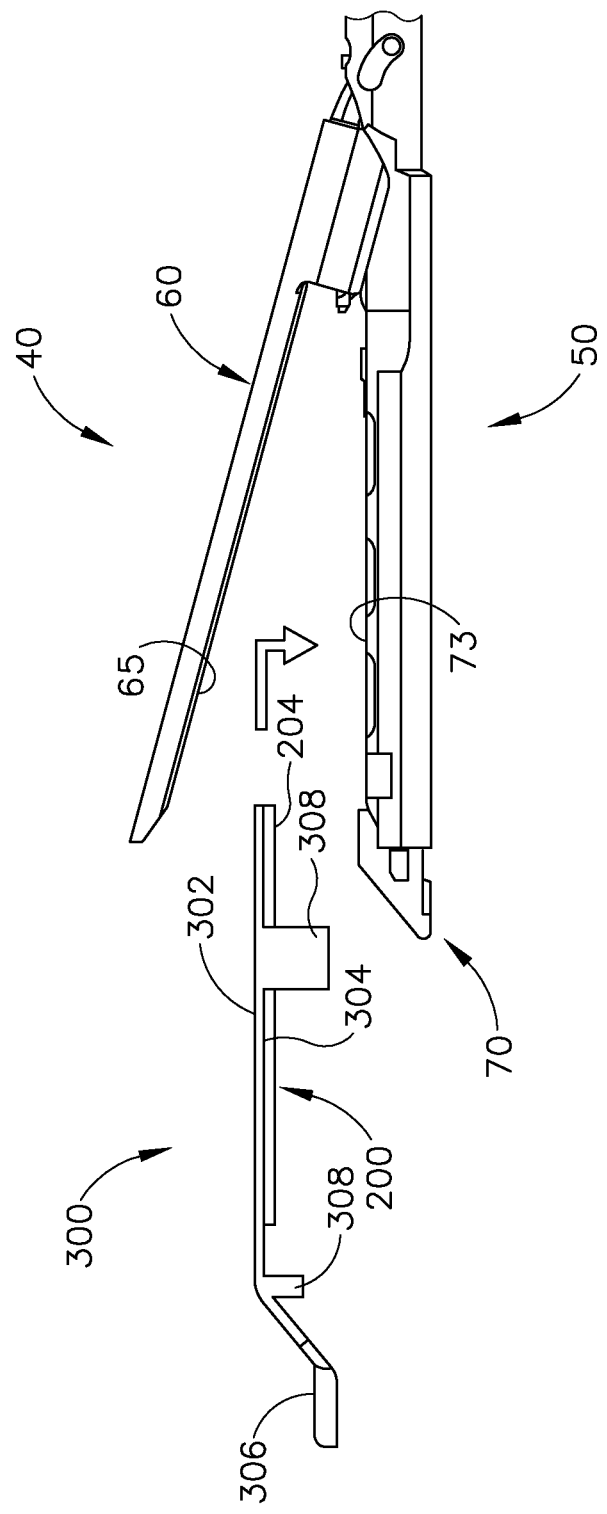
FIG. 12A depicts a side elevational view of the buttress and retainer of FIG. 10 positioned for engagement with the end effector of FIG. 3.
Figure 12D:
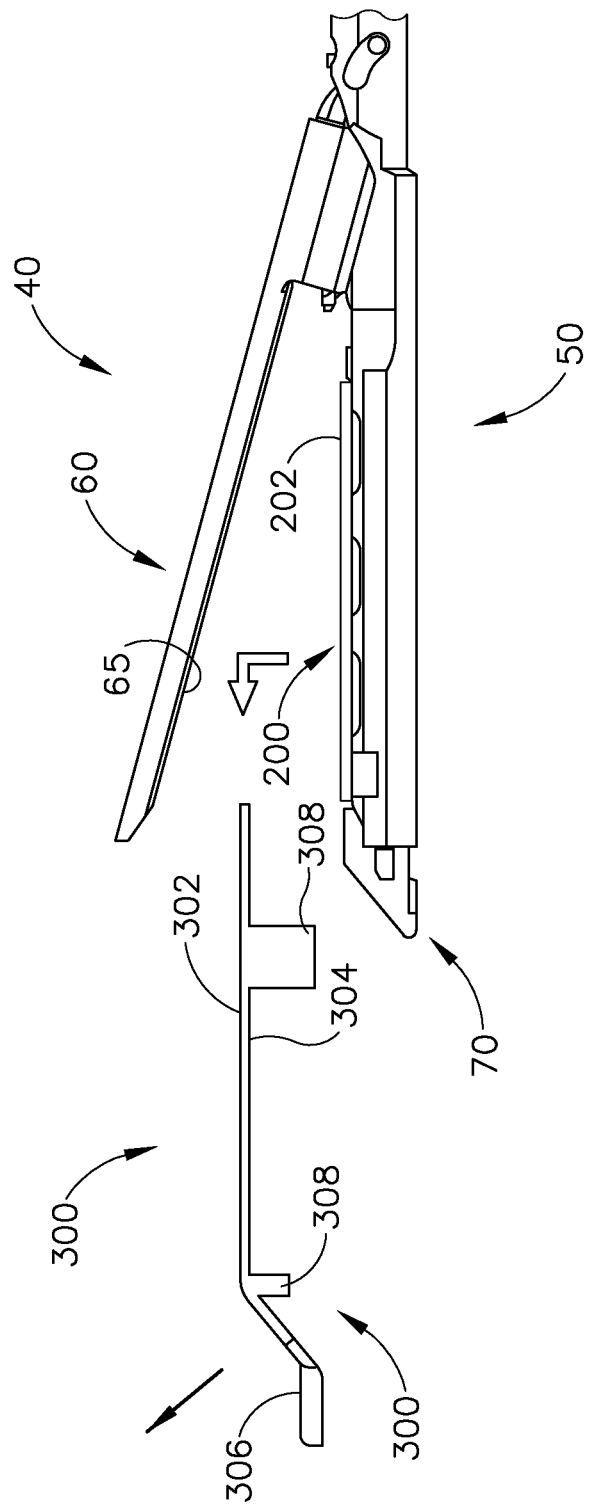
FIG. 12D depicts a side elevational view of the retainer of FIG. 10 being moved away from the end effector of FIG. 3, with the buttress of FIG. 10 being left behind on the end effector to form an end effector and buttress assembly.

As shown in FIG. 12A, the assembly formed by buttress (200) and retainer (300) may be placed before end effector (40) with anvil (60) in the open position. In some instances, a peel-away film (not shown) is positioned over underside (204) of buttress (200) to protect buttress (200) and/or any adhesive material on underside (204) of buttress (200). In such versions, the film is peeled away to expose underside (204) of buttress (200) before reaching the stage shown in FIG. 12A. Such a film may comprise polytetrafluoroethylene (PTFE) and/or any other suitable material(s). After reaching the stage shown in FIG. 12A, the assembly formed by buttress (200) and retainer (300) may then be placed on staple cartridge (70) such that underside (204) of buttress (200) apposingly contacts deck (73) of staple cartridge (70); and such that latches (308) are releasably secured to lower jaw (50) as shown in FIG. 12B. The operator may then drive anvil (60) toward the closed position as shown in FIG. 12C, eventually compressing buttress (200) against deck (73) of staple cartridge (70). Such compression may promote adhesion between underside (204) of buttress (200) and deck (73) of staple cartridge (70). After anvil (60) has been used to compress buttress (200) against deck (73) of staple cartridge (70), anvil (60) may be moved back to the open position as shown in FIG. 12D. As also shown in FIG. 12D, retainer (300) may then be pulled away from end effector (40), leaving behind buttress (200) adhered to deck (73) of staple cartridge (70). Upper side (202) of buttress (200) is exposed. End effector (40) is thus loaded with buttress (200) and ready for use in severing and stapling tissue (90).

Figure 14:
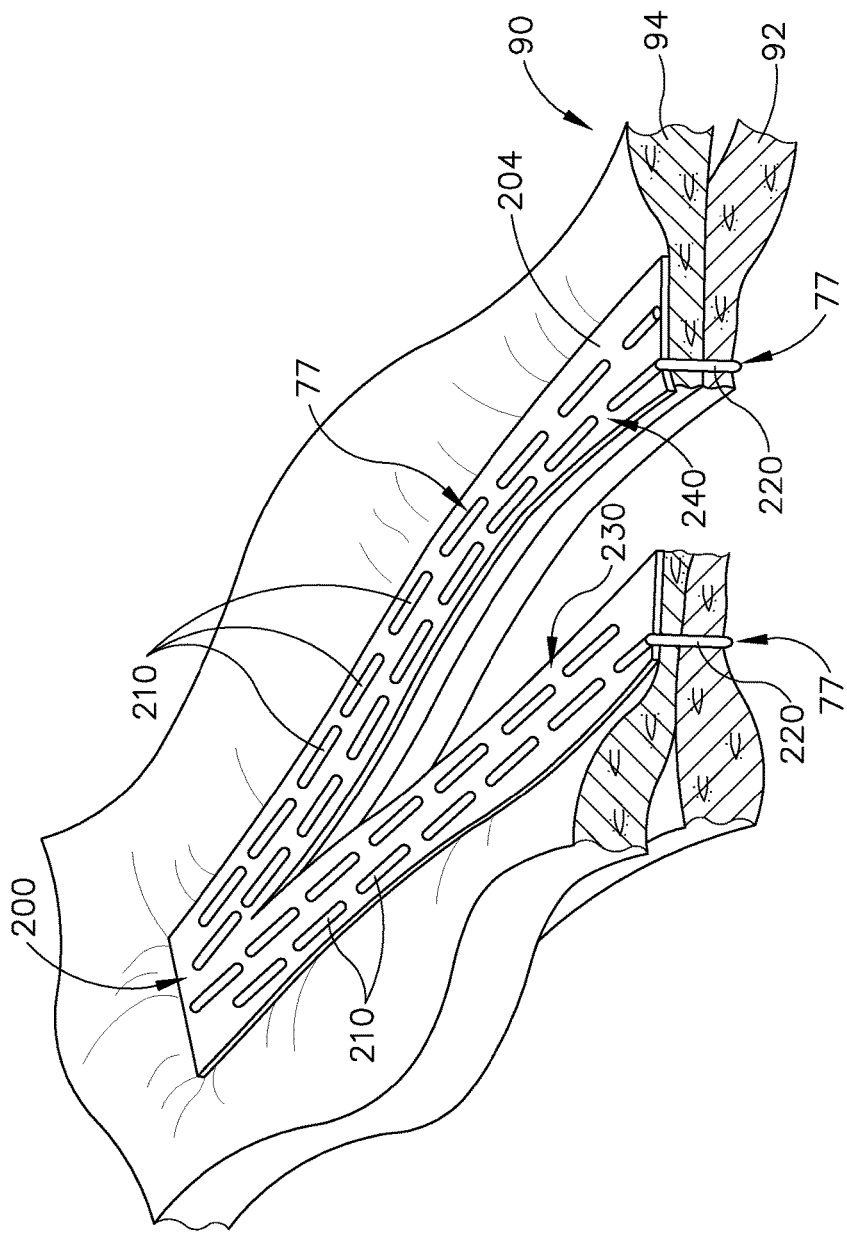
FIG. 14 depicts a perspective view of staples and the buttress of FIG. 12D having been secured to tissue by the end effector of FIG. 12D.
Figure 15:
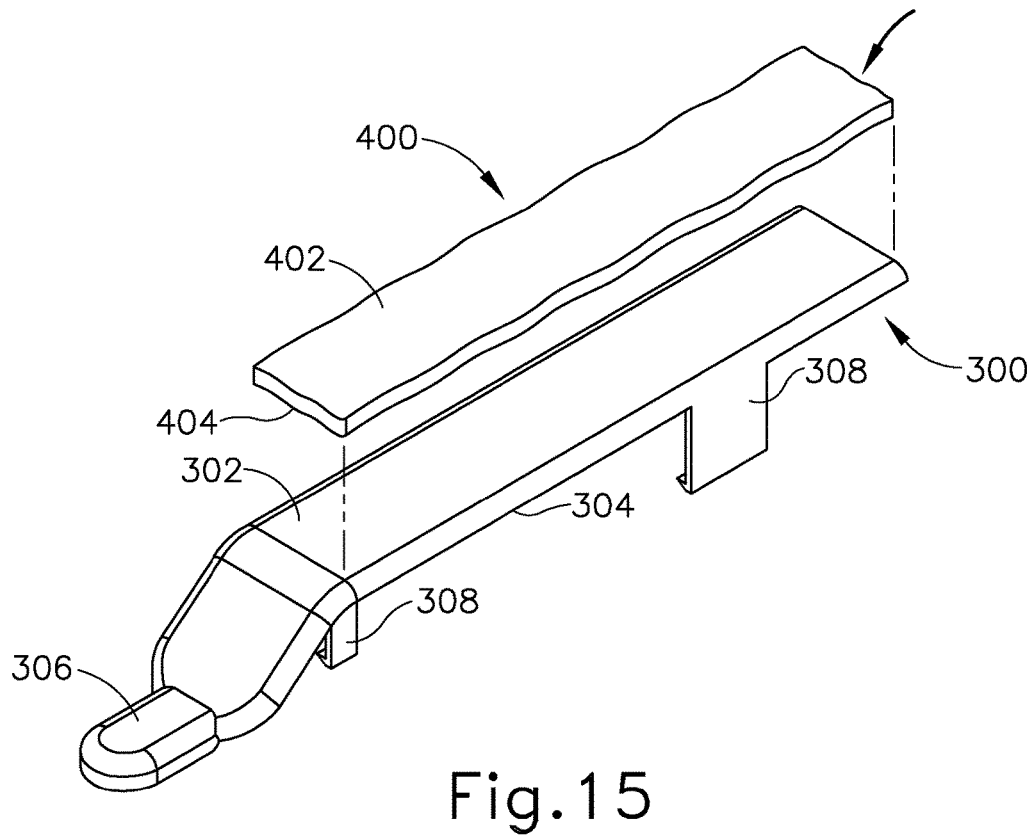
FIG. 15 an exploded perspective view of an exemplary buttress and retainer.
Figure 16:
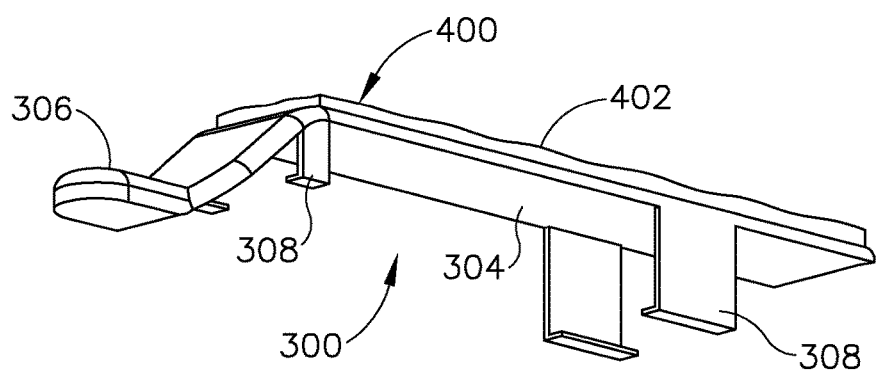
FIG. 16 depicts a perspective view of the buttress and retainer of FIG. 15, with the buttress secured to the top side of the retainer.

FIGS. 13A-13C show an end effector (40) loaded with buttress (200) being used to drive a staple (77) through tissue (90). In FIG. 13A, tissue (90) is placed between anvil (60) and staple cartridge (70), above buttress (200), with anvil (60) in the open position. In FIG. 13B, anvil (60) is driven to the closed position, compressing tissue (90) against buttress (200) and staple cartridge (70). End effector (40) is then actuated as described above, driving staple (77) through buttress (200) and tissue (90). As shown in FIG. 13C, crown (210) of driven staple (77) captures and retains buttress (200) against layer (94) of tissue (90). It should be understood that a series of staples (77) will similarly capture and retain buttress (200) against layer (94) of tissue (90), thereby securing buttress (200) to tissue (90) as shown in FIG. 14. As end effector (40) is pulled away from tissue (90) after deploying staples (77) and buttress (200), buttress (200) disengages deck (73) of staple cartridge (70), such that buttress (200) remains secured to tissue (90) with staples (77). Buttress (200) thus provides structural reinforcement to the lines of staples (77). As can also be seen in FIG. 14, knife member (80) also cuts through a centerline of buttress (200), separating buttress (200) into two sections (230, 240), such that each section (230, 240) remains secured to a respective severed region of tissue (90).

C. Exemplary Instrument and Technique for Securing Buttress to Anvil of End Effector FIGS. 15-17B show a combination of an exemplary buttress (400) with retainer (300). Buttress (400) of this example may be constructed in accordance with the teachings above relating to buttress assembly (100) and/or in accordance with other teachings herein. Buttress (400) includes an upper side (402) and an underside (404). In the present example, upper side (402) includes an adhesive (e.g., like upper adhesive layer (1064) to secure buttress (200) to underside (65) of anvil (60) as described in greater detail below.

In the present example, buttress (400) is secured to upper side (302) of retainer (300), such that underside (404) of buttress (400) apposes upper side (302) of retainer (300). In some versions, an adhesive such as lower adhesive layer (106) provides releasable adhesion of buttress (400) to upper side (302) of retainer (300). In some other versions, retainer (300) includes one or more features (e.g., flanges, clips, etc.) that are configured to selectively retain buttress (400) against upper side (302) of retainer (300). Various suitable ways in which buttress (200) may be releasably secured to upper side (302) of retainer (300) will be apparent to those of ordinary skill in the art in view of the teachings herein.

Figure 17A:
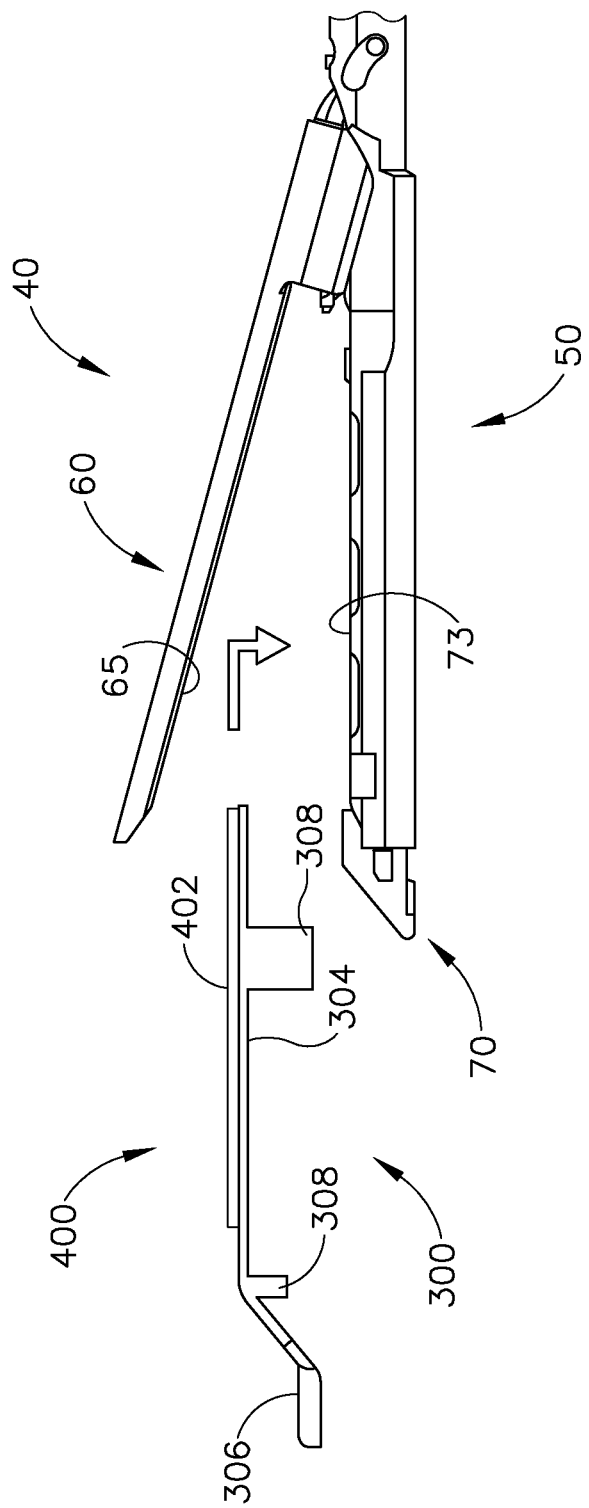
FIG. 17A depicts a side elevational view of the buttress and retainer of FIG. 15 positioned for engagement with the end effector of FIG. 3.
Figure 17B:
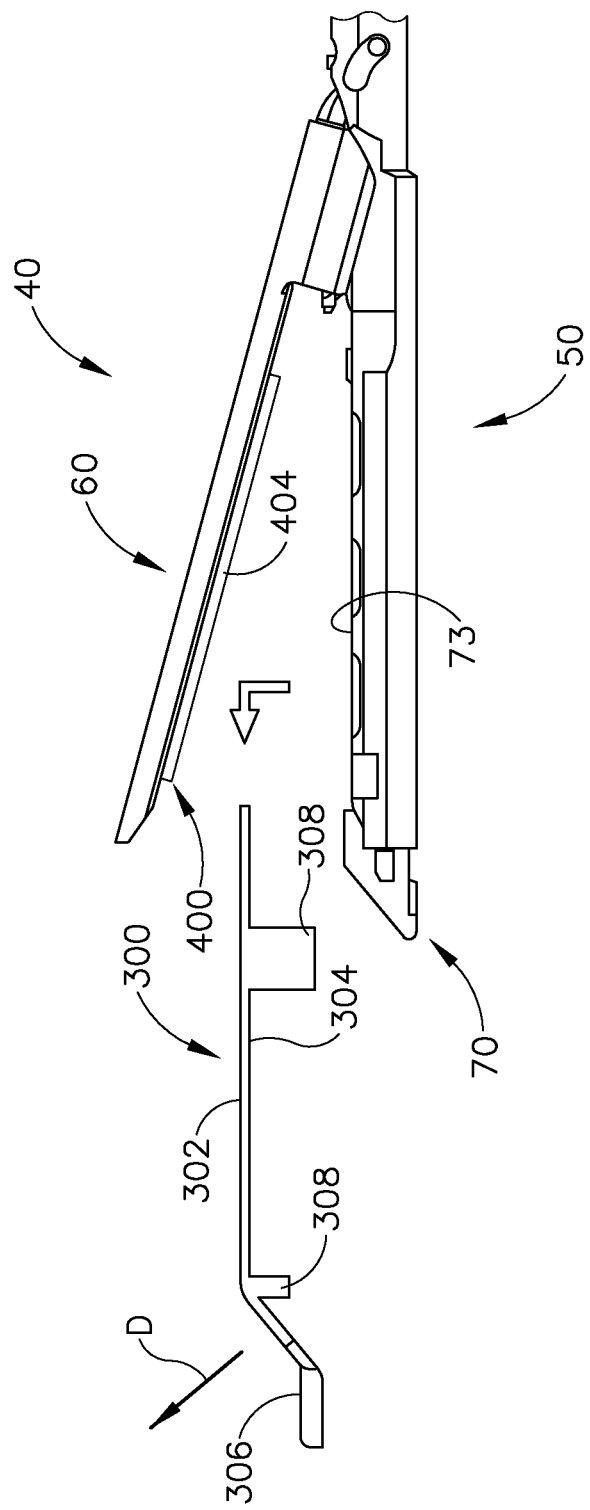
FIG. 17B depicts a side elevational view of the retainer of FIG. 15 being moved away from the end effector of FIG. 3, with the buttress of FIG. 15 being left behind on the end effector to form an end effector and buttress assembly.

As shown in FIG. 17A, the assembly formed by buttress (400) and retainer (300) may be placed before end effector (40) with anvil (60) in the open position. In some instances, a peel-away film (not shown) is positioned over upper side (402) of buttress (400) to protect buttress (400) and/or any adhesive material on upper side (402) of buttress (400). In such versions, the film is peeled away to expose upper side (402) of buttress (400) before reaching the stage shown in FIG. 17A. Such a film may comprise polytetrafluoroethylene (PTFE) and/or any other suitable material(s). After reaching the stage shown in FIG. 17A, the assembly formed by buttress (400) and retainer (300) may then be placed on staple cartridge (70) such that latches (308) are releasably secured to lower jaw (50) as described above. The operator may then drive anvil (60) toward the closed position as described above, eventually compressing buttress (400) underside (65) of anvil (60). Such compression may promote adhesion between upper side (402) of buttress (400) and underside (65) of anvil (60). After anvil (60) has been used to compress buttress (200) against underside (65) of anvil (60), anvil (60) may be moved back to the open position as shown in FIG. 17B. As also shown in FIG. 17B, retainer (300) may then be pulled away from end effector (40), leaving behind buttress (400) adhered to underside (65) of anvil (60). Underside (402) of buttress (400) is exposed. End effector (40) is thus loaded with buttress (400) and ready for use in severing and stapling tissue (90).

Figure 19:
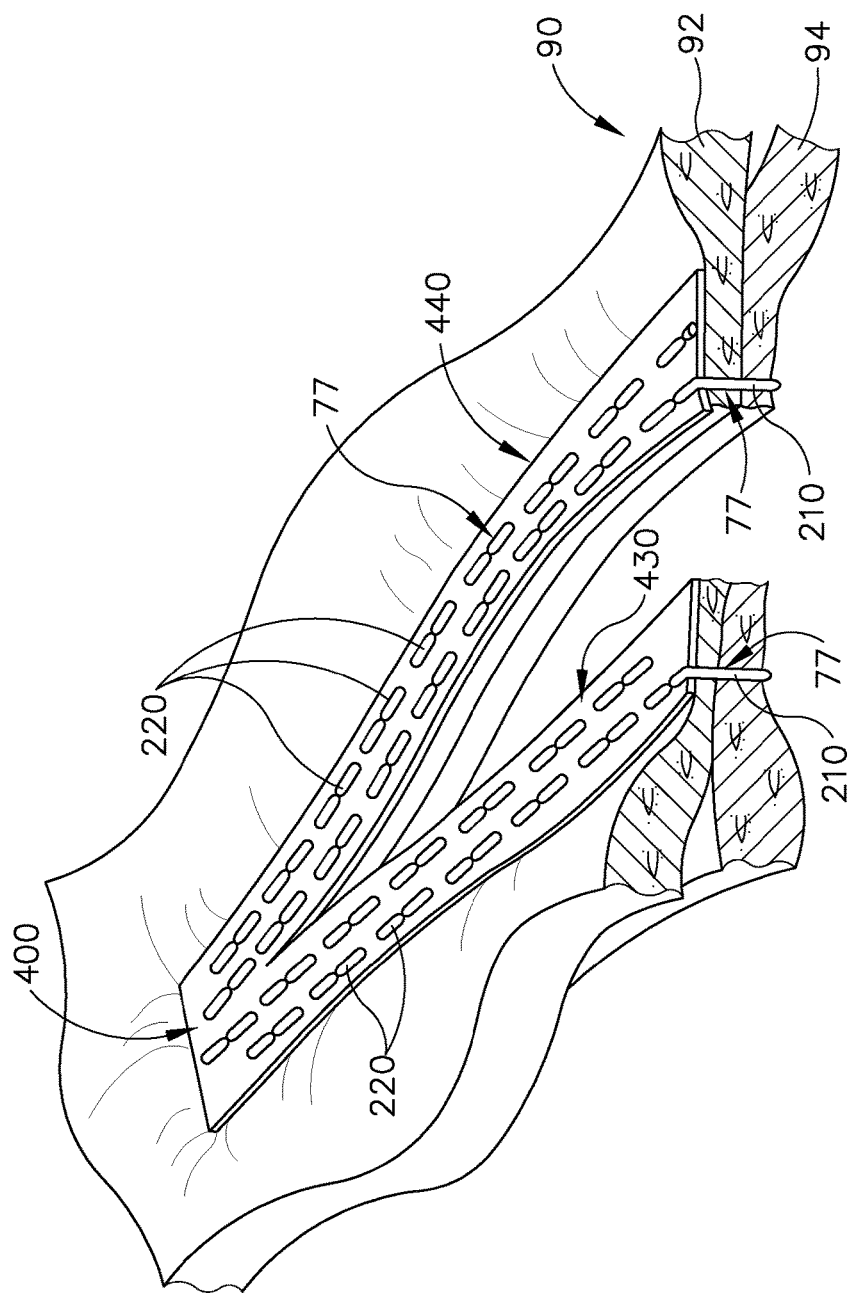
FIG. 19 depicts a perspective view of staples and the buttress of FIG. 17B having been secured to tissue by the end effector of FIG. 17B.

FIGS. 18A-18C show an end effector (40) loaded with buttress (400) being used to drive a staple (77) through tissue (90). In FIG. 18A, tissue (90) is placed between anvil (60) and staple cartridge (70), below buttress (400), with anvil (60) in the open position. In FIG. 18B, anvil (60) is driven to the closed position, compressing tissue (90) against buttress (400) and staple cartridge (70). End effector (40) is then actuated as described above, driving staple (77) through buttress (400) and tissue (90). As shown in FIG. 18C, bent legs (220) of driven staple (77) capture and retains buttress (400) against layer (92) of tissue (90). It should be understood that a series of staples (77) will similarly capture and retain buttress (400) against layer (92) of tissue (90), thereby securing buttress (400) to tissue (90) as shown in FIG. 19. As anvil (60) is returned to the open position to enable end effector (40) to be pulled away from tissue (90) after deploying staples (77) and buttress (400), buttress (400) disengages underside (65) of anvil (60), such that buttress (400) remains secured to tissue (90) with staples (77). Buttress (400) thus provides structural reinforcement to the lines of staples (77). As can also be seen in FIG. 19, knife member (80) also cuts through a centerline of buttress (400), separating buttress (400) into two sections (430, 440), such that each section (430, 440) remains secured to a respective severed region of tissue (90).

While the examples above provide either buttress (200) on underside (304) of retainer (300) or buttress (400) on upper side (302) of retainer (300), it should be understood that both retainers (200, 400) may be provided on the same retainer (300) if desired. In particular, retainer (200) may be provided on underside (304) of retainer (300) while buttress (400) is provided on upper side (302) of retainer (300). This may result in buttress (200) being provided on deck (73) of staple cartridge (70) and buttress (400) being provided on underside (65) of anvil (60) in the same end effector (400). This may ultimately result in buttress (200) being secured against layer (94) of tissue (90) by crowns (210) of staples (77) while buttress (400) is secured against layer (92) of tissue (90) by bent legs (220) of the same staples (77).

III. Exemplary Materials and Techniques for Providing Adhesion of Buttress to Surgical Stapler As noted above, a buttress assembly (100) may include at least one layer (104, 106) of adhesive material (or other form of adhesive material) that adheres buttress body (102) to either underside (65) of anvil (60) or deck (73) of staple cartridge (70). Such an adhesive material may provide proper positioning of buttress body (102) before and during actuation of end effector (40); then allow buttress body (102) to separate from end effector (40) after end effector (40) has been actuated, without causing damage to buttress body (102) that is substantial enough to compromise the proper subsequent functioning of buttress body (102). It may be desirable to minimize the impact of such an adhesive material on the functioning of firing beam (82) wedge sled (78), and staple drivers (75). For instance, it may be desirable to prevent the adhesive material from blocking or otherwise providing significant resistance to movement of firing beam (82) wedge sled (78), and staple drivers (75). Moreover, the adhesive material should allow buttress body (102) to detach easily enough from an actuated end effector (40) to avoid tearing tissue (90) after staples (77) have been fired through the tissue and anvil (60) is moved to the open position.

In some instances, it may be desirable for the adhesive material to provide additional effects, beyond merely adhering buttress body (102) to either underside (65) of anvil (60) or deck (73) of staple cartridge (70). For instance, the adhesive material may include one or more components that provide a therapeutic effect, hemostatic effect, or other desired effect on tissue (90). As another merely illustrative example, the adhesive material may fill in at least part of the paths that are formed through tissue (90) and/or buttress body (102) by legs (220) of staple (77) being driven through tissue (90) and buttress body (102).

In some instances, the adhesive material for a buttress body (102) may be pressure sensitive. In addition or in the alternative, the adhesive material may be configured to take the form of surface irregularities of buttress body (102); in addition to or in lieu of taking the form of surface irregularities in underside (65) of anvil (60) and/or deck (73) of staple cartridge (70).

The above noted characteristics of an adhesive material for a buttress body (102) are merely illustrative examples. Suitable adhesive materials may possess various other characteristics in addition to or in lieu of those above. Suitable adhesive materials may also be provided in various different kinds of compositions. Examples of various suitable compositions and configurations that may be used to form and provide an adhesive material for a buttress body (102), as well as various exemplary characteristics that such adhesive material may possess, are described in greater detail below.

A. Exemplary Polymeric Adhesive Materials with Synthetic Base

In some instances, an adhesive material (e.g., one or more of layers (104, 106)) for a buttress body (102) comprises an absorbable synthetic based polymer. Various physiomechanical properties of synthetic based polymers may be modified in order to provide different adhesive properties. Such variable characteristics include but are not limited to copolymer composition, glass transition temperature (Tg), molecular weight, inherent viscosity (IV), crystallinity, sequence distribution, copolymer chain composition, melting temperature (Tm), and surface tension. Several exemplary combinations of these variables will be provided below, though it should be understood that these examples are merely illustrative. It should also be understood that these examples of adhesive materials may be provided in upper adhesive layer (104). In addition or in the alternative, these examples of adhesive materials may be provided in lower adhesive layer (106). In addition or in the alternative, these examples of adhesive materials may be otherwise integrated into buttress body (102). It should therefore be understood that the adhesive material need not necessarily constitute a separate layer that is discretely identifiable as being different from a layer defined by buttress body (102).

In some examples, the adhesive material is formed by a copolymer of lactide and caprolactone (PLA/PCL). This composition may be provided at a ratio in the range of 20/80 to 60/40; or more particularly the range of 35/65 to 50/50. This composition may have a glass transition temperature (Tg) that is below 4° C., or more particularly below −10° C. This composition may have a molecular weight in the range of 10,000 g/mol to 145,000 g/mol; or more particularly below 200,000 g/mol. The composition may have an inherent viscosity (IV) in the range of 1.0 dL/g to 2.0 dL/g.

In some other examples, the adhesive material is formed by a copolymer of lactide and trimethylene carbonate (PLA/TMC). This composition may be provided at a ratio in the range of 20/80 to 50/50. The other characteristics may be within the same parameters set forth above with respect to the exemplary PLA/PCL composition. Alternatively, the PLA/TMC composition may have any other suitable characteristics.

In some other examples, the adhesive material is formed by a copolymer of trimethylene carbonate and caprolactone (TMC/PCL). This composition may be provided at a ratio in the range of 20/80 to 80/20; or more particularly in the range of 50/50 to 60/40. This composition may have an inherent viscosity (IV) in the range of 0.3 dL/g to 3.0 dL/g; or more particularly in the range of 0.5 dL/g to 1.0 dL/g. This composition may have a crystallinity below 20%; or more particularly below 5%; or more particularly at 0% (i.e., a completely amorphous polymer). This composition may have a glass transition temperature (Tg) below 0° C.; or more particularly below −20° C.

In some other examples, the adhesive material is formed by a copolymer of caprolactone and glycolide (PCL/PGA). This composition may be provided at a ratio in the range of 45/55 to 85/15; or more particularly in the range of 40/60 to 65/35; or more particularly in the range of 50/50 to 65/35. This composition may have an inherent viscosity (IV) in the range of 0.2 dL/g to 3.0 dL/g; or more particularly in the range of 1.0 dL/g to 2.0 dL/g. This composition may have a molecular weight in the range of 100,000 g/mol to 200,000 g/mol. This composition may have a crystallinity below 20%; or more particularly below 5%; or more particularly at 0% (i.e., a completely amorphous polymer). This composition may have a glass transition temperature (Tg) below 0° C.; or more particularly below −20° C. One particular example of this composition has a ratio of 50/50 PCL/PGA; an inherent viscosity (IV) of 0.2; a molecular weight of 83,000 g/mol; and a glass transition temperature (Tg) of −19.4°. Another particular example of this composition has a ratio of 65/35 PCL/PGA; an inherent viscosity (IV) of 1.04 to 1.07; a molecular weight of 110,000 g/mol to 118,000 g/mol; and a glass transition temperature (Tg) in the range of −37.3° to −38.6°.

Other exemplary synthetic based polymer compositions that may be used to form the adhesive material include the following: propanediol and caprolactone (PDO/PCL); a combination of propanediol, caprolactone, and trimethylene carbonate (PDO/PCL/TMC), with very low to no crystallinity and a glass transition temperature (Tg) below 0° C.; and a homopolymer poly(TMC), with an inherent viscosity (IV) of approximately 0.5 dL/g. Other suitable synthetic based polymer compositions will be apparent to those of ordinary skill in the art in view of the teachings herein.

The adhesive material may include a blocky copolymer. For instance, one example of a blocky copolymer that may be used in the adhesive material comprises blocky poly (TMC), with a low glass transition temperature (Tg). In some instances, the blocky copolymer may be randomized. In some other instances, such as when the copolymer is amorphous (e.g., 0% crystallinity), the blocky copolymer may be ordered.

The adhesive material may include various kinds of copolymer chain compositions. For instance, the copolymer chain composition may be branched with relatively short segments. This may further enhance the malleability experience. Alternatively, the copolymer chain may be linear. As another alternative, the copolymer may be cross-linked or star pattern. However, in versions where the copolymer is cross-linked, it may be desirable for the base copolymer segments to be more amorphous the more that those segment are cross-linked.

As noted above, the melting temperature (Tm) is a physiomechanical property of a polymer that may be selected to provide desired adhesive characteristics. In some instances, the lower melting temperature (Tm) of a monomer component could limit the amount of the co-monomer needed to create a desired adhesive effect. By way of example only, polydioxanone (PDS) has a melting temperature (Tm) around approximately 110° C. and a glass transition temperature (Tg) around approximately −10° C. Thus, polydioxanone (PDS) may need less caprolactone (PCL) to make a suitable pressure sensitive adhesive (PSA) copolymer. It should also be understood that polydioxanone (PDS) copolymers with polyglycolide (PGA) or lactide (PLA) may provide desired adhesive effects. It may be desirable for such copolymers to have a glass transition temperature (Tg) that is below room temperature; a melting temperature (Tm) that is at or below room temperature; a crystallinity in the range of 10% to 0%; and an inherent viscosity (IV) that is less than 2.0 dL/g, or more particularly less than 1.0 dL/g.

In some examples the adhesive material may comprise a blended copolymer. For instance, the high and low molecular weight of the same pressure sensitive adhesive (PSA) copolymer may allow for the degradation rate to be adjusted without adjusting the polymer chemistry. As the low molecular weight version breaks down, its acid byproducts would then change the pH and effect the breakdown of the high molecular weight parts. Preferred blends of copolymers would include those that will not affect the crystallinity, low melting temperature (Tm), and low glass transition temperature (Tg) of the copolymers.

Some examples of the adhesive material may comprise polyurethane. For instance, the polyurethane may be provided as a pressure sensitive adhesive (PSA). By of example only, polyurethane based pressure sensitive adhesives (PSAs) may be prepared from isocyanates, polyols, and chain extenders. Pressure sensitive adhesives (PSAs) may also be prepared from 100% solids, waterborne, or solvent borne systems. The properties of polyurethane based pressure sensitive adhesives (PSAs) may be controlled by varying the ratio of isocyanates to polyols and chain extenders. As another merely illustrative example, the polyurethane may be provided in a flowable form. For instance, a flowable polyurethane based adhesive material may have an inherent viscosity (IV) that is less than 1.0 dL/g, or more particularly less than 0.5 dL/g; a glass transition temperature (Tg) that is in the range of −10° C. and 10° C.; or more particularly closer to −10° C.; and a consistency similar to that of honey or oil, if desired, with the proper inherent viscosity (IV).

The foregoing examples of absorbable synthetic based polymers are provided for merely illustrative purposes. Other suitable examples will be apparent to those of ordinary skill in the art in view of the teachings herein. It should also be understood that the foregoing examples of absorbable synthetic based polymers may be readily incorporated into the various teachings and examples provided below. In other words, the foregoing examples of absorbable synthetic based polymers may be readily incorporated into any example herein that refers to an adhesive material.

B. Exemplary Polymeric Adhesive Materials with Natural Base

While the above discussion provides various examples of synthetic based polymers that may be used as an adhesive material (e.g., one or more of layers (104, 106)) for a buttress body (102), it should also be understood that a natural based polymer may be used as an adhesive material. Several merely illustrative examples of natural based polymers that may be used as an adhesive material will be described in greater detail below. It should also be understood that these examples of adhesive materials may be provided in upper adhesive layer (104). In addition or in the alternative, these examples of adhesive materials may be provided in lower adhesive layer (106). In addition or in the alternative, these examples of adhesive materials may be otherwise integrated into buttress body (102). It should therefore be understood that the adhesive material need not necessarily constitute a separate layer that is discretely identifiable as being different from a layer defined by buttress body (102).

In some instances, the adhesive material comprises a hydrogel. The hydrogel may generally comprise a hydrophilic polymer network capable of absorbing and/or retaining fluids. An exemplary hydrogel material is glycol methacrylate. By way of further example only, suitable hydrogel materials may comprise homopolymer hydrogels, copolymer hydrogels, multipolymer hydrogels, interpenetrating polymer hydrogels, and combinations thereof. In further examples, the hydrogel may comprise microgels, nanogels, and combinations thereof. The hydrogel may further comprise a non-crosslinked hydrogel, a crosslinked hydrogel, and combinations thereof. The hydrogel may comprise chemical crosslinks, physical crosslinks, hydrophobic segments and/or water insoluble segments. The hydrogel may be chemically crosslinked by polymerization, small-molecule crosslinking, and/or polymer-polymer crosslinking.

The hydrogel may be physically crosslinked by ionic interactions, hydrophobic interactions, hydrogen bonding interactions, sterocomplexation, and/or supramolecular chemistry. The hydrogel may be substantially insoluble due to the crosslinks, hydrophobic segments and/or water insoluble segments, but be expandable and/or swellable due to absorbing and/or retaining fluids. In some versions, the precursor may crosslink with endogenous materials and/or tissues.

Further examples of hydrogels that may be used include multifunctional acrylates, hydroxyethylmethacrylate (HEMA), and elastomeric acrylates. In additional or in the alternative, a hydrogel adhesive material may be constructed in accordance with at least some of the teachings of U.S. Pat. Pub. No. 2012/0241492, entitled "Tissue Thickness Compensator Comprising at Least One Medicament," published Sep. 27, 2012, now U.S. Pat. No. 9,839,420, issued Dec. 12, 2017, the disclosure of which is incorporated by reference herein. Other suitable ways in which an adhesive material may be provided with hydrogel will be apparent to those of ordinary skill in the art in view of the teachings herein.

Further examples of naturally based polymers that may be used to form an adhesive material include alginate (e.g., calcium alginate, calcium sodium alginate, etc.); hyaluronic acid, collagen (including gelatin), and polysaccharide. In versions including a polysaccharide, the polysaccharide may include cellulose, chitin, pectin, or arabinoxylans. In versions including cellulose, the cellulose may comprise oxidized regenerated cellulose, carboxy-methylcellulose, carboxyethyl cellulose, hydroxypropyl cellulose, hydroxyethyl cellulose, or oxidized cellulose. In versions including chitin, the chitin may comprise chitosan (e.g., deacetylated chitin) or chitosan salts.

Some versions of naturally based polymers that may be used to form an adhesive material may include a putty or wax-like material. Some such versions may be non-absorbable and may be similar to a conventional bone wax. For instance, the material may comprise beeswax with one or more of the paraffin, petroleum jelly, isopropyl palmitate, sesame oil, carbolic acid; or any other conventional bone wax composition. Some other versions of a putty or wax-like material that may be used to form an adhesive material for buttress body (102) may be absorbable or resorbable. For instance, some such versions may comprise HEMASORB® putty by Abyrx, Ink of Irvington, N.Y., water-soluble alkylene copolymers (e.g., OSTENE by Baxter Healthcare Corporation of Deerfield, Ill.), glycerol, 1-lactide, glycolide, polyethylene glycol (PEG), polyethylene oxide (PEO), or polyolefin elastomer (POE). By way of further example, the adhesive material may comprise polyethylene glycol (PEG) or a polyethylene glycol (PEG) copolymer with a molecular weight of less than 20,000 g/mol. Having the molecular weight in such a range may promote passage of the dissolved form of the adhesive through the kidneys. See, e.g., Webster et al., "PEGylated Proteins: Evaluation of Their Safely in the Absence of Definitive Metabolism Studies," *Drug Metabolism and Disposition*, Vol. 35, No. 1, pp. 9-16 (2007), the disclosure of which is incorporated by reference herein. As yet another merely illustrative example, the adhesive material may be constructed in accordance with at least some of the teachings of U.S. Pat. No. 2,642,375, entitled "Hemostatic Compositions," issued Jun. 16, 1953, the disclosure of which is incorporated by reference herein.

Some polymer adhesives, including but not limited to the putty or wax-like compositions referred to above, may include oxidized regenerated cellulose (ORC), which is a hemostatic agent. For instance, a putty or wax-like composition may serve as a carrier for oxidized regenerated cellulose (ORC). U.S. Patent Pub. No. 2012/0241493, entitled "Tissue Thickness Compensator Comprising Controlled Release and Expansion," published Sep. 27, 2012, the disclosure of which is incorporated by reference herein, discusses various ways in which oxidized regenerated cellulose (ORC) may be incorporated into various compositions. It should be understood that such teachings of U.S. Patent Pub. No. 2012/0241493 may be readily applied herein in the context of incorporating oxidized regenerated cellulose (ORC) into polymer adhesives, including but not limited to the putty or wax-like compositions referred to above.

The foregoing examples of natural based polymers are provided for merely illustrative purposes. Other suitable examples will be apparent to those of ordinary skill in the art in view of the teachings herein. It should also be understood that the foregoing examples of natural based polymers may be readily incorporated into the various teachings and examples provided below. In other words, the foregoing examples of natural based polymers may be readily incorporated into any example herein that refers to an adhesive material.

C. Exemplary Malleable Bioabsorbable Polymer Adhesive

In some instances, it may be desirable to provide one or more adhesive layers (104, 106) with a malleable bioabsorbable polymer adhesive. Such a polymer may be highly viscous yet still flowable at room temperature. A malleable polymer adhesive may, in response to pressure being applied to it, take the form of a surface with which it is engaged. In other words, if a malleable polymer adhesive is pressed against deck (73) of staple cartridge (70), the malleable polymer adhesive may take the form of the one or more features of the deck (73) that it the malleable polymer adhesive is pressed against. Similarly, if a malleable polymer adhesive is pressed against underside (65) of anvil (60), the malleable polymer adhesive may take the form of the one or more features of underside (65) that it the malleable polymer adhesive is pressed against. By deforming to the geometry that it is pressed against, the malleable polymer adhesive may adhere to the geometry; and may further provide re-applyable attachment. If the desired positioning of buttress assembly (100) on deck (73) or underside (65) is not achieved, the malleable polymer adhesive may permit buttress assembly (100) to be removed, repositioned, and re-adhered to deck (73) or underside (65). It should be understood that the examples provided below may be malleable at room temperature, such that additional heating or other treatment is not necessary in order to provide malleability.

Providing the adhesive material in the form of a malleable polymer may minimize the impact of fluids and debris on the adhesion of buttress assembly (100) to deck (73) of staple cartridge (70) or underside (65) of anvil (60). The malleable polymer adhesive material may also be hydrophilic (e.g., at least in certain regions of buttress assembly (100)), encouraging adhesion in a wet environment. In addition or in the alternative, adhesive layer (104, 102) of buttress assembly (100) may include a combination of adhesive material and hydrophobic material in respective localized regions. The hydrophobic material may drive fluids out of the adhesion areas, thereby improving adhesion at the localized regions of adhesive material.

In some instances, when a buttress assembly (100) having a malleable bioabsorbable polymer adhesive is sterilized using ethylene oxide at a high temperature, the ethylene oxide gas may act as a plasticizer, increasing the fluidic aspects of the adhesive. Buttress assembly (100) may include features that are configured to contain the adhesive at this stage (and/or at other stages where the adhesive may become more fluidic), to maintain the adhesive properties of the adhesive later in its life cycle. For instance, such containment features may be provided by buttress body (102). In addition or in the alternative, such containment features may be provided by a peel away film layer that is provided on the opposite side of adhesive layer (104, 106), such that the adhesive layer (104, 106) is interposed between buttress body (102) and the peel away film layer. Such a peel away film layer may comprise recesses or cavities, etc., as features that provide a predefined space where the viscous fluid adhesive may be retained. Other suitable forms of adhesive retention features will be apparent to those of ordinary skill in the art in view of the teachings herein.

The below examples include various compositions of malleable bioabsorbable polymer adhesives and various exemplary configurations through which a malleable bioabsorbable polymer adhesive may be combined with a buttress body (102). In the present example, it is contemplated that the adhesive material comprises a synthetic based polymer such as those referred to herein. However, it should also be understood that naturally based polymers may be incorporated with the below teachings. It should also be understood that, even if some of the below examples are provided specifically in the context of being applied to just deck (73) of staple cartridge (70), the same examples may be readily applied to underside (65) of anvil (60). Similarly, to the extent that some of the below examples are provided specifically in the context of being applied to just underside (65) of anvil (60), the same examples may be readily applied to deck (73) of staple cartridge (70).

1. Exemplary Compositions Providing Malleable Absorbable Polymer Adhesive

In some versions, the polymer adhesive is provided in a thin layer having properties in the range of malleable to flowable (high viscosity), with a tacky surface contact. In some versions, such polymer adhesives have a low inherent viscosity (IV) with low crystallinity. One such composition may comprise a 65/35 copolymer of caprolactone and glycolide (PCL/PGA). Another such composition may comprise a 65/35 copolymer of trimethylene carbonate and caprolactone (TMC/PCL). Another such composition may comprise a 75/25 copolymer of lactide and caprolactone (PLA/PCL). Another such composition may comprise a copolymer of trimethylene carbonate and lactide (TMC/PLA).

It should also be understood that some of the putty or wax-like compositions previously referred to may be used to provide a malleable polymer adhesive. Absorbable versions of such compositions include HEMASORB® putty by Abyrx, Ink of Irvington, N.Y., water-soluble alkylene copolymers (e.g., OSTENE by Baxter Healthcare Corporation of Deerfield, Ill.), glycerol, 1-lactide, glycolide, and polyethylene glycol (PEG). Non-absorbable versions of such compositions include beeswax with one or more of the paraffin, petroleum jelly, isopropyl palmitate, sesame oil, carbolic acid; or any other conventional bone wax composition. Some malleable polymer adhesives, including but not limited to the putty or wax-like compositions, may include oxidized regenerated cellulose (ORC), as further noted above.

The foregoing are just a few merely illustrative examples of malleable polymer compositions that may be used to adhere buttress body (102) to underside (65) of anvil (60) or deck (73) of staple cartridge (70). By way of further example only, other suitable compositions may include various other compositions referred to herein and variations thereof.

2. Exemplary Structural Configurations Incorporating a Malleable Absorbable Polymer Adhesive with a Buttress There are a variety of structural configurations that may be used to incorporate a malleable absorbable polymer adhesive with a buttress body (102) to form a buttress assembly (100) that may be adhered to underside (65) of anvil (60) or deck (73) of staple cartridge (70). Several merely illustrative examples are described in greater detail below. Further examples will be apparent to those of ordinary skill in the art in view of the teachings herein. It should also be understood that, while the following examples are provided as separate examples, the concepts and features of the following examples may be combined with each other in numerous ways as will be apparent to those of ordinary skill in the art in view of the teachings herein.

a. Thin Film Malleable Polymer Adhesive on Buttress

A malleable absorbable polymer adhesive may be provided as a thin film on buttress body (102). In one merely illustrative example, a copolymer adhesive film layer (104, 106) is compression molded in a 65/35 caprolactone and glycolide (PCL/PGA) form to a thickness in the range of 75 mils to 250 mils. The compressed adhesive film layer (104, 106) can then be pressed into adhesive contact with buttress body (102). A polytetrafluoroethylene (PTFE) film may be applied to the exposed face of adhesive film layer (104, 106) to protect the face of adhesive film layer (104, 106). Right before the resulting buttress assembly (100) is to be applied to deck (73) of staple cartridge (70) or underside (65) of anvil (60), the polytetrafluoroethylene (PTFE) film may be removed to expose the adhesive film layer (104, 106). The exposed adhesive film layer (104, 106) may then be pressed against deck (73) of staple cartridge (70) or underside (65) of anvil (60), thereby adhering buttress assembly (100) to deck (73) of staple cartridge (70) or underside (65) of anvil (60).

In another merely illustrative example, a fluidic composition of 50/50 caprolactone and glycolide (PCL/PGA) is heated and painted onto buttress body (102), thereby providing a thin adhesive film layer (104, 106). As the film adhesive film layer (104, 106) cools to room temperature, the adhesive film layer (104, 106) behaves like a thick compressed film element to adhere to deck (73) of staple cartridge (70) or underside (65) of anvil (60). As described above, a polytetrafluoroethylene (PTFE) film may be used to selectively protect and expose the adhesive film layer (104, 106).

In versions where a malleable absorbable polymer adhesive is provided as a thin film on buttress body (102), it should be understood that adhesion may occur as the thin adhesive film layer (104, 106) is deformed due to compression against deck (73) of staple cartridge (70) or underside (65) of anvil (60). The adhesive film layer (104, 106) has a tacky surface condition but the adhesion may actually be provided through a combination of cohesion, surface tension, deformation of the contact surface to mate directly to the geometry of deck (73) of staple cartridge (70) or underside (65) of anvil (60), and some tacky adhesion, rather than just adhesion alone.

b. Openings Formed Through Malleable Polymer Adhesive Layer to Limit Migration

Figure 20:
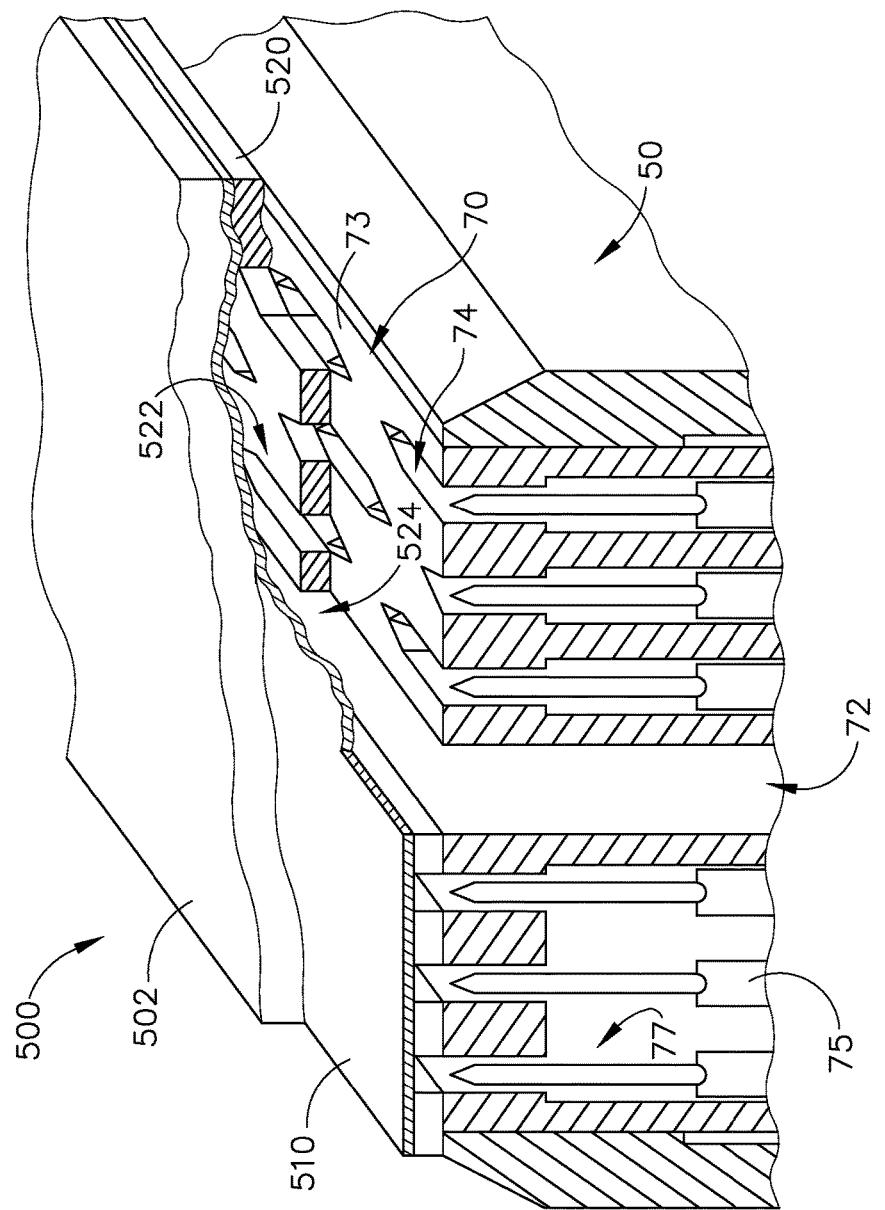
FIG. 20 depicts a partial, cross-sectional, perspective view of a staple cartridge with an exemplary buttress assembly secured thereto.
Figure 21:
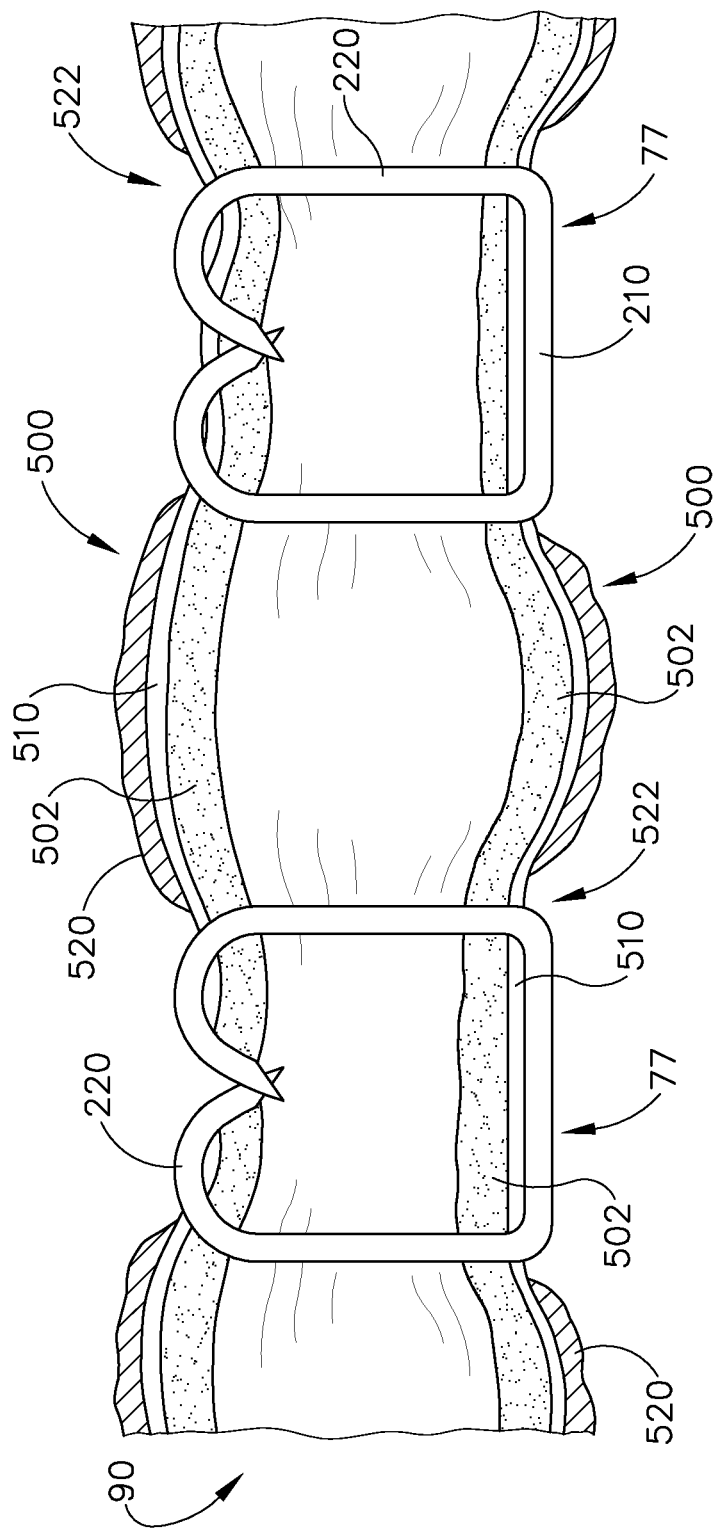
FIG. 21 depicts a cross-sectional view of staples and a buttress secured to tissue.

In some versions, buttress assembly (100) includes a geometry and/or other features that improve adhesion and/or prevent inadvertent flow of adhesive material into undesirable regions. FIGS. 20-21 show an exemplary buttress assembly (500) that is configured to provide such properties.

Buttress assembly (500) of this example comprises a buttress body (502), an intermediate layer (510), and an adhesive layer (520). Buttress body (502) may be configured and operable just like buttress body (102) described above. Adhesive layer (520) may comprise any of the various adhesive materials referred to herein, including but not limited to any of the various absorbable malleable polymer compositions.

Intermediate layer (510) is interposed between buttress body (502) and adhesive layer (520). At least a portion of intermediate layer (510) may be impermeable or semi impermeable as described above, to prevent or restrict migration of adhesive material from adhesive layer (520) into buttress body (502). Intermediate layer (510) is configured to promote and prevent adhesion of the material forming adhesive layer (520) at different regions. In particular, as best seen in FIG. 20, in which buttress assembly (500) is applied to a deck (73) of a staple cartridge (70), adhesive layer (520) includes an opening (522) over each staple pocket (74) of staple cartridge (70). Openings (522) are configured to prevent the material forming adhesive layer (520) from entering or otherwise covering staple pockets (74), thereby preventing the adhesive layer from inhibiting the exit of staples (77) from staple pockets (74). Adhesive layer (520) further includes an opening (524) in the form of a longitudinal channel over channel (72) of staple cartridge (70). Opening (524) is configured to prevent the material forming adhesive layer (520) from entering or otherwise covering channel (72), thereby preventing the adhesive layer from inhibiting the distal motion of firing beam (82) through channel (72). In instances where buttress assembly (500) is applied to underside (65) of anvil (60), openings (522) may be sized and positioned to prevent the material forming adhesive layer (520) from entering or otherwise covering staple forming pockets (64). Similarly, opening (524) may be configured to prevent the material forming adhesive layer (520) from entering or otherwise covering channel (62).

In the present example, openings (522, 524) are formed due to the presence of features of intermediate layer (510) that are configured to prevent adhesion of the adhesive material. In other words, when the adhesive material is applied to intermediate layer during the process of forming adhesive assembly (500), those features of intermediate layer keep the adhesive material away from the regions where openings (522, 524) are intended to be formed. By way of example only, such features may comprise a micro and/or macro surface finish features and/or other kinds of features. As another merely illustrative example, intermediate layer (510) may comprise macro standing features that keep the adhesive material away from the regions where openings (522, 524) are intended to be formed. As yet another merely illustrative example, a die or other device may be used to keep the adhesive material away from the regions where openings (522, 524) are intended to be formed. Such a die may be removed at any suitable time before buttress assembly (500) is applied to deck (73) of staple cartridge (70) or underside (65) of anvil (60). Other suitable ways in which openings (522, 524) may be formed will be apparent to those of ordinary skill in the art in view of the teachings herein. It should also be understood that intermediate layer (510) may include a surface finish and/or other surface features that is/are configured to promote adhesion of the adhesive material to the regions outside of openings (522, 524).

FIG. 21 shows an example of a set of staples (77) driven through tissue (90), with two buttress assemblies (500) secured to the tissue (90). In this example, one buttress assembly (500) had been secured to deck (73) of staple cartridge (70) while another buttress assembly (500) had been secured to underside (65) of anvil (60). As can be seen, openings (522) are sized to accommodate staples (77) at each buttress assembly (500). Thus, neither crowns (210) nor legs (220) of staples (77) have passed through any of the material forming adhesive layer (520) in either buttress assembly (500).

c. Malleable Polymer Adhesive Rods

Figure 22A:
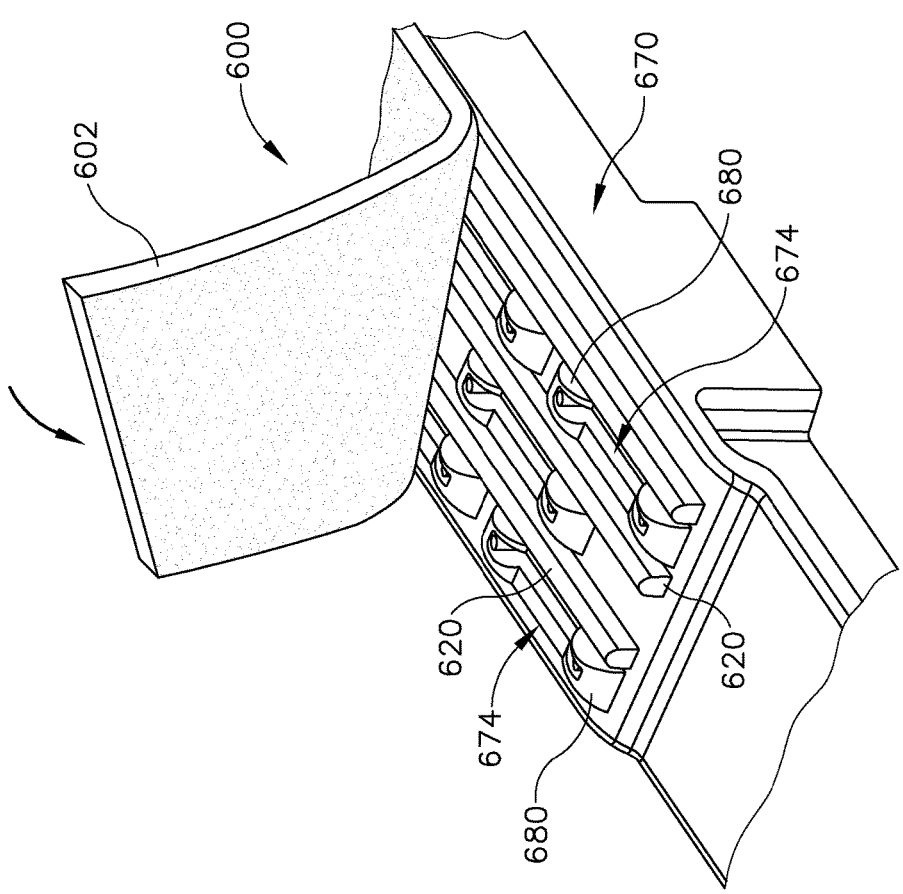
FIG. 22A depicts a partial perspective view of a staple cartridge with a buttress being laid over exemplary retention features.
Figure 22B:
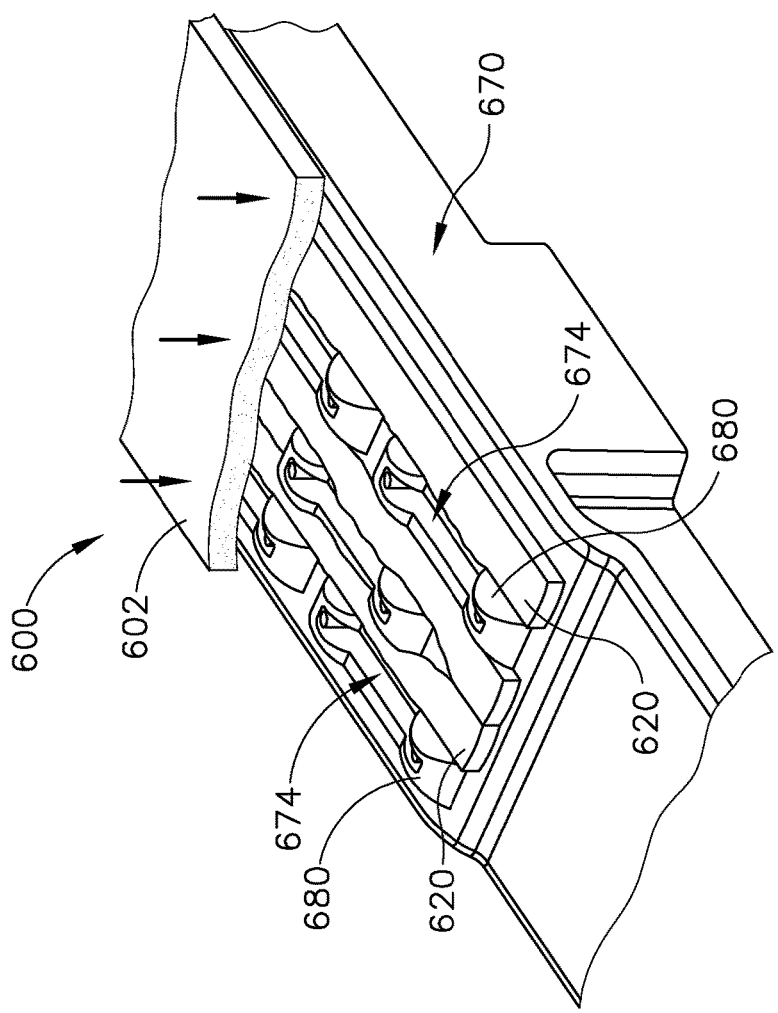
FIG. 22B depicts a partial perspective view of the staple cartridge of FIG. 22A, with the buttress being pressed against the retention features to thereby secure the buttress to the staple cartridge.

FIGS. 22A-22B show an exemplary buttress assembly (600) comprising a buttress body (602) and a set of adhesive rods (620). Buttress body (602) may be configured and operable just like buttress body (102) described above. Adhesive rods (620) may comprise any of the various adhesive materials referred to herein, including but not limited to any of the various absorbable malleable polymer compositions. By way of specific example only, adhesive layer (620) may comprise one of the putty or wax-like compositions previously referred to.

Buttress assembly (600) is shown as being used in combination with a staple cartridge (670) that is substantially similar to staple cartridge (70). However, staple cartridge (670) of this example comprises upwardly extending, U-shaped lip members (680) around the end of each staple pocket (674). Staple cartridge (670) is otherwise identical to staple cartridge (70).

Figure 23:
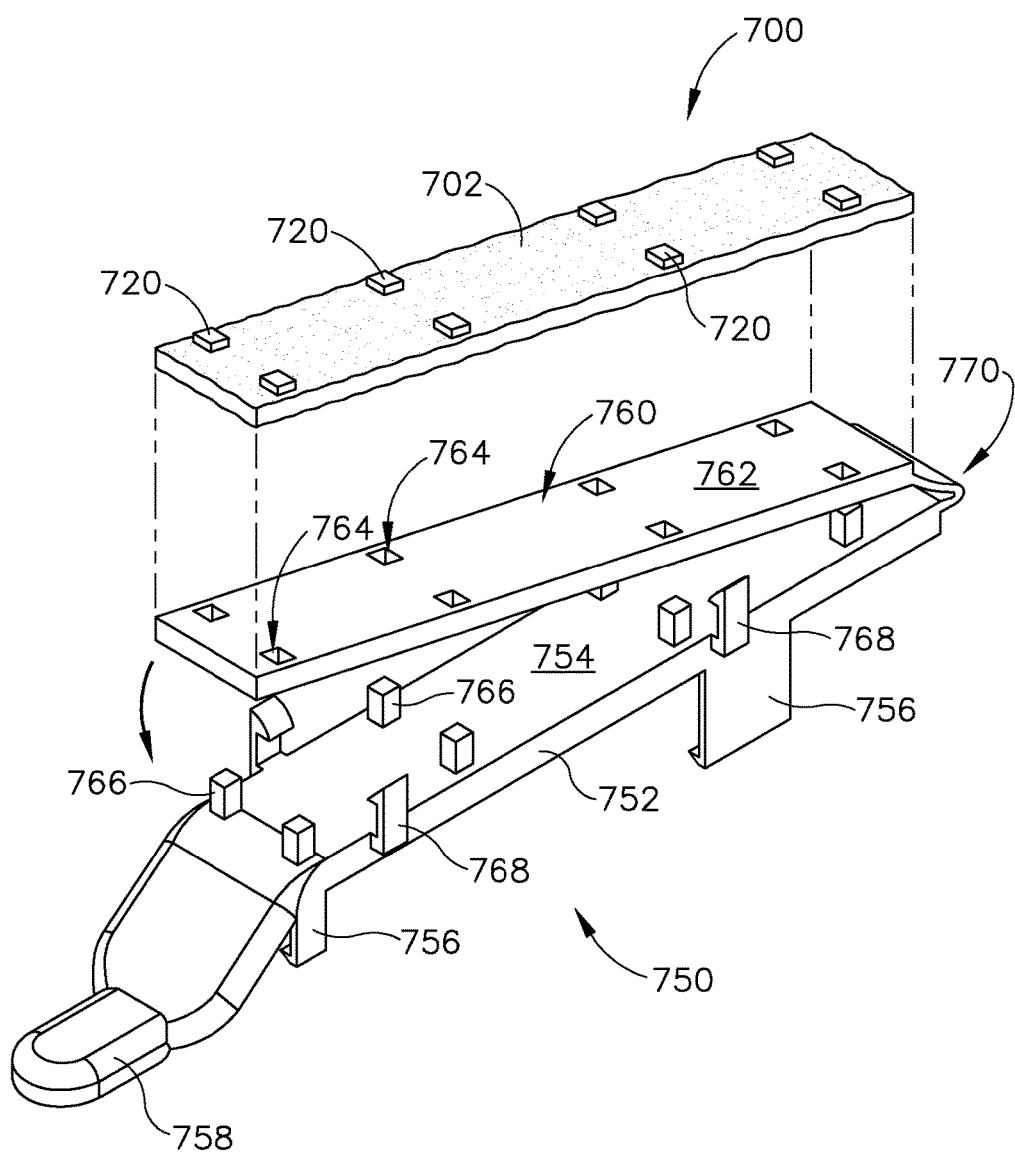
FIG. 23 depicts an exploded perspective view of an exemplary alternative retainer with a buttress positioned for engagement with an upper portion of the retainer.

Adhesive rods (620) are oriented to extend longitudinally, such that adhesive rods are parallel to each other and parallel to the longitudinal axis defined by staple cartridges (70). Adhesive rods (620) are positioned laterally between lip members (680), such that lip members (680) are configured to maintain the positioning of adhesive rods (620). During an initial stage of applying buttress assembly (600) as shown in FIG. 22A, to deck (674) of staple cartridge (670), adhesive rods (620) are cylindrical in form, each having a substantially circular cross section. Buttress body (602) is then pressed against adhesive rods (520), causing adhesive rods (620) to malleably deform as shown in FIG. 22B. This malleable deformation adheres buttress body (602) to deck (674) of staple cartridge (670). Lip members (680) prevent the material forming adhesive rods (620) from entering or otherwise blocking staple pockets (674) during and after this deformation of adhesive rods (620). With buttress body (602) secured to deck (674) of staple cartridge (670) by malleably deformed adhesive rods (620), the end effector that is equipped with staple cartridge (670) and buttress assembly (600) is ready for use as described herein. It should be understood that, with lip members (680) shielding staple pockets (674) from the adhesive material forming adhesive rods (620), the staples driven from staple cartridge (670) will not pass through the adhesive material when staple cartridge (670) is actuated. It should also be understood that adhesive rods (620) (or adhesive structures that are similar to adhesive rods (620) may be positioned on underside (65) of anvil (60) to secure a buttress body (602) to underside (65) of anvil (60). Such adhesive rods (620) may be laterally positioned between longitudinally extending rows of staple forming pockets (64).

d. Discrete Regions of Malleable Polymer Adhesive with Retainer Having Adhesive Driving Features FIG. 23 shows an exemplary alternative buttress assembly (700) with an exemplary alternative retainer (750). Buttress assembly (700) of this example comprises a buttress body (702) and a plurality of discretely formed adhesive regions (720). Buttress body (702) may be configured and operable just like buttress body (102) described above. Adhesive regions (720) may comprise any of the various adhesive materials referred to herein, including but not limited to any of the various absorbable malleable polymer compositions. In the present example, adhesive regions (720) are square shaped, though it should be understood that adhesive regions (720) may have any other suitable configuration.

Retainer (750) comprises a base member (752) having an upper surface (754), a plurality of latches (756), and a distally projecting tongue (758) that is configured to facilitate grasping and manipulation of retainer (750). Retainer (750) also includes an upper member (760) that is secured to base member (752) by a living hinge (770). Upper member (760) has an upper surface (762) that is configured to engage buttress body (702). A plurality of openings (764) are formed through upper member (760). Openings (764) are configured and arranged to correspond with the configuration and arrangement of adhesive regions (720) when buttress assembly (700) is laid over upper surface (762). A plurality of rigid posts (766) extend upwardly from upper surface (754) of base member (752). Posts (766) are configured and arranged to correspond with the configuration and arrangement of openings (764) and adhesive regions (720).

Figure 24:
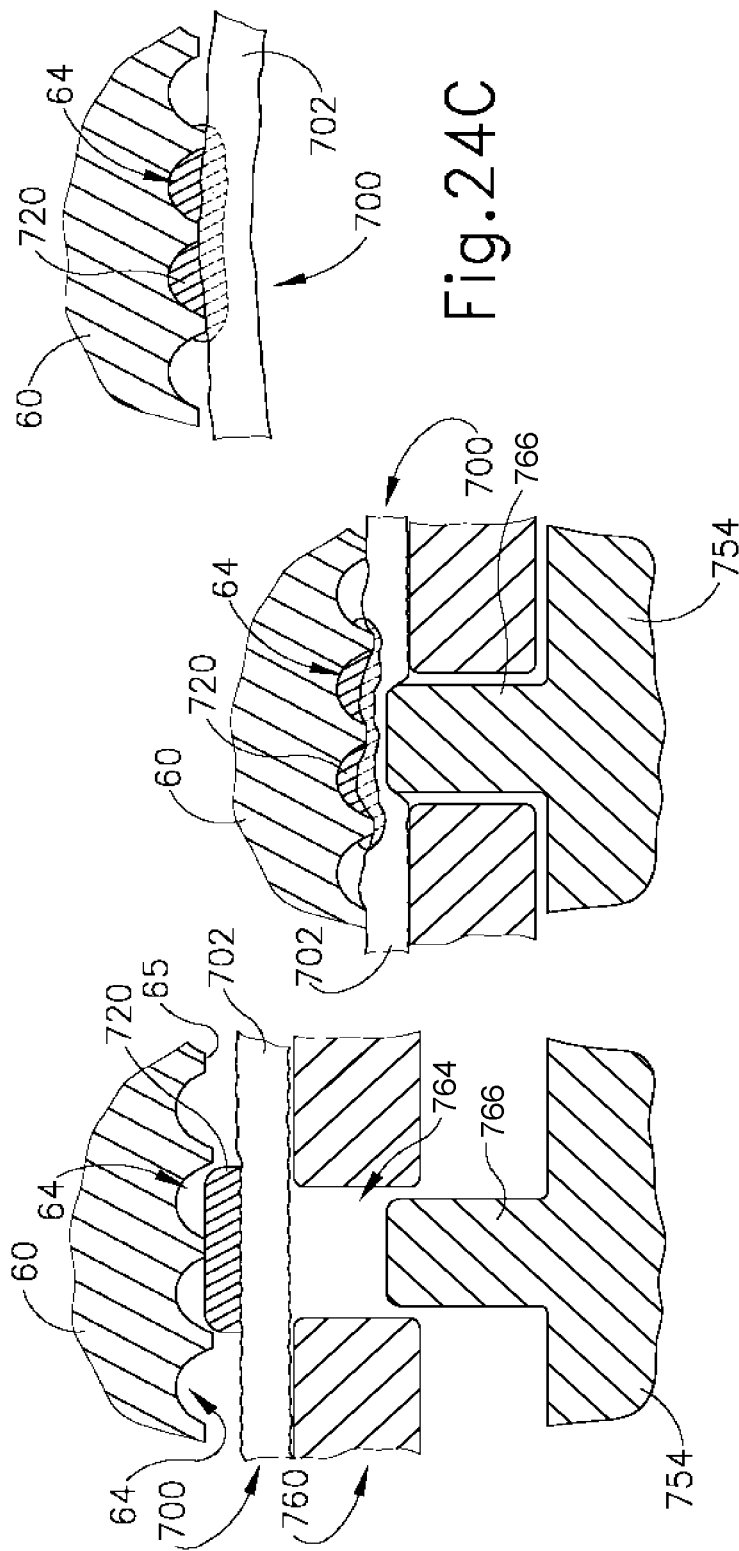
FIG. 24A depicts a cross-sectional view of the retainer and buttress of FIG. 23, with an adhesive portion of the buttress positioned to contact the anvil of the end effector of FIG. 3, and with a post of the retainer spaced away from the buttress.
FIG. 24B depicts a cross-sectional view of the retainer and buttress of FIG. 23, with the post of the retainer driving the adhesive portion of the buttress into the anvil.
FIG. 24C depicts a cross-sectional view of the buttress of FIG. 23 adhered to the anvil of the end effector of FIG. 3, with the retainer removed.

It should be understood that retainer (750) may be removably secured to end effector (40) in a manner similar to retainer (300) described above, with latches (756) releasably engaging lower jaw (50). At such a stage, upper member (760) is spaced away from upper surface (754) of base member (752) due to a resilient bias imposed by living hinge (770). Retainer (750) may thus be configured as shown in FIG. 24A, where anvil (60) is brought into initial contact with buttress assembly (700). As shown, an adhesive region (720) of buttress assembly (700) is positioned directly under a pair of staple forming pockets (64). Alternatively, adhesive region (720) may be positioned under some other feature of underside (65) of anvil (60). The resilient bias provided by living hinge (770) ensures that adhesive region (720) contacts the appropriate region of underside (65) of anvil (60) before anvil (60) reaches a fully closed position. The resilient bias provided by living hinge (770) may also provide and maintain a minimum consistent pressure during the closure of anvil (60) to enhance the attachment of adhesive region (720) to underside (65) of anvil (60).

As anvil (60) is driven further toward the closed position, anvil (60) bears down on adhesive region (720) and upper member (760), thereby causing upper member (760) to pivot toward base member (752). As upper member (760) pivots toward base member (752), post (764) passes through opening (762). The height of post (764) is greater than the vertical thickness of upper member (760), such that the top of post (764) protrudes above upper surface (762) of upper member (760) when upper member (760) is driven downwardly into apposition with upper surface (754) of base member (752). The protruding top of post (764) provides an opposing force against the underside of buttress body (702), in the region beneath adhesive region (720). Adhesive region (720) is thus compressed between underside (65) of anvil (60) and the region of buttress body (702) just above the top of post (764). This compression results in malleable deformation of adhesive region (720), such that the material forming adhesive region takes the form of the corresponding staple forming pockets (64), as shown in FIG. 24B.

Figure 25:
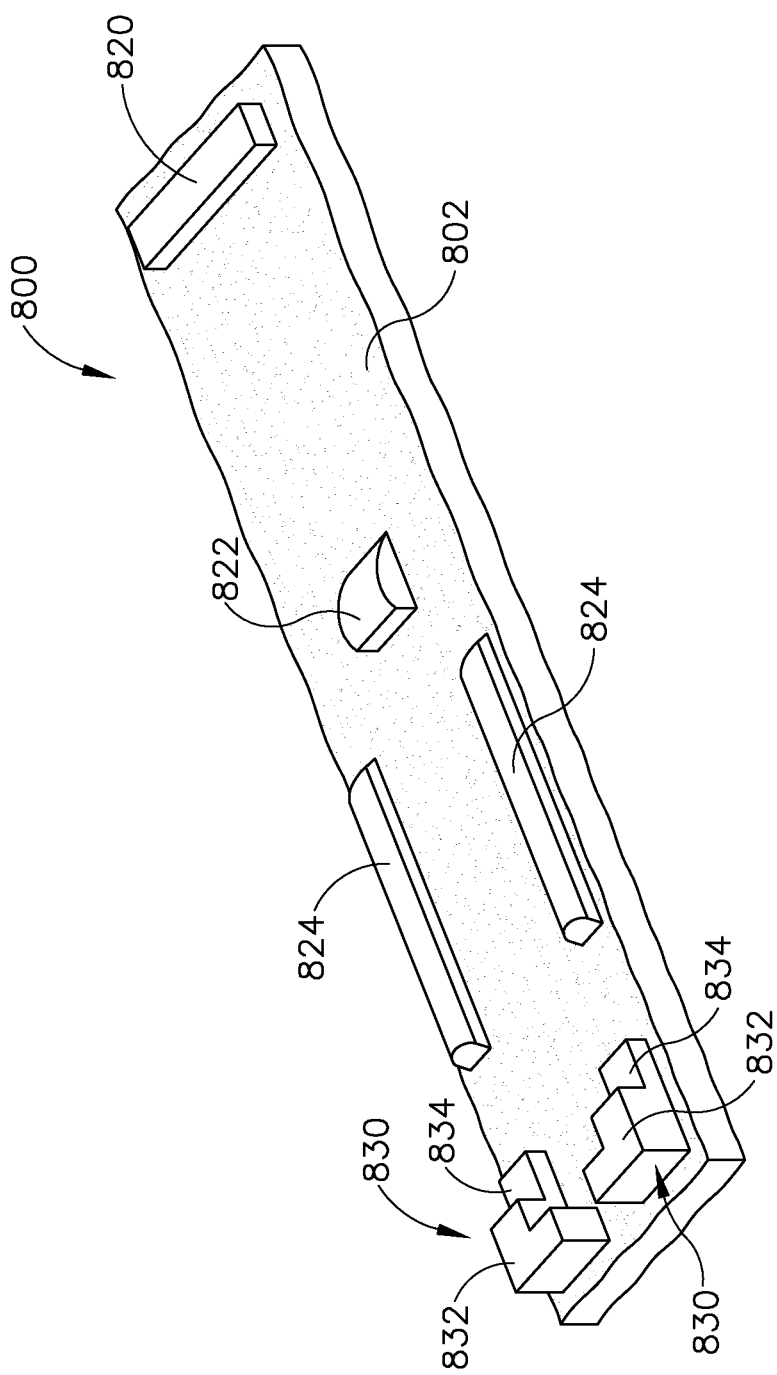
FIG. 25 depicts a perspective view of an exemplary alternative buttress assembly.

It should be understood that the foregoing actions may take place at every post (764) and adhesive region (720), such that the adhesive regions (720) together adhere buttress assembly (700) to underside (65) of anvil (60). At this stage, latches (768) of retainer (750) may secure upper member (760) into apposition with base member (752), facilitating removal of retainer (750) from end effector (40). Buttress assembly (700) is left adhered to underside (65) of anvil (60) as shown in FIG. 24C, such that end effector (40) is then ready for use.

e. Buttress Assembly with Malleable Polymer Adhesive in Asymmetric Geometries and Thicknesses FIG. 25 shows an exemplary buttress assembly (800) comprising a buttress body (802) and a plurality of adhesive regions (820, 822, 824, 830). Buttress body (802) may be configured and operable just like buttress body (102) described above. Adhesive regions (820, 822, 824, 830) may comprise any of the various adhesive materials referred to herein, including but not limited to any of the various absorbable malleable polymer compositions. A first adhesive region (820) extends laterally along a proximal portion of buttress body (802), spanning substantially the full width of buttress body (802). A second adhesive region (822) is located near the longitudinal and lateral center of buttress body (802). Third and fourth adhesive regions (824) extend longitudinally along each lateral side of buttress body (802). Fifth and sixth adhesive regions (830) are located at the distal end of buttress body (802), at the corners. Each adhesive region (830) includes a thick portion (832) and a thin portion (834). It should be understood that any of the other adhesive regions (822, 824, 830) may also have thick and thin portions. In addition or in the alternative, some adhesive regions (820, 822, 824, 830) may be thicker than other adhesive regions (820, 822, 824, 830). In addition or in the alternative, some adhesive regions (820, 822, 824, 830) may have a greater density than other adhesive regions (820, 822, 824, 830). Similarly, any one of the adhesive regions (820, 822, 824, 830) may have varying intra-region density.

It should be understood that providing varying thicknesses and/or densities among and/or within adhesive regions (820, 822, 824, 830) may result in a non-homogenous pressure distribution on adhesive regions (820, 822, 824, 830) when buttress assembly (800) is pressed against deck (73) of staple cartridge (70) or underside (65) of anvil (60). Such non-homogenous pressure distribution may maximize bonding in certain areas while letting other areas have less deformation and adhesion. Other suitable ways in which a buttress assembly may be formed with varying thicknesses and/or densities among and/or within adhesive regions will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler end effector, the end effector comprising: (a) a staple cartridge, wherein the staple cartridge comprises: (i) a plurality of staples, and (ii) a deck, wherein the staple cartridge is operable to drive the staples through the deck; (b) an anvil, wherein the anvil is movable from an open position toward the staple cartridge to reach a closed position, wherein the anvil includes an underside having staple forming surface configured to receive staples driven through the deck; and (c) a buttress assembly, wherein the buttress assembly comprises: (i) a buttress body, and (ii) an adhesive material, wherein the adhesive material is configured to removably secure the buttress body to the deck of the staple cartridge or the underside of the anvil, wherein the adhesive material comprises a polymer, wherein the polymer is malleable, wherein the polymer is bioabsorbable.

Example 2

The surgical stapler end effector of Example 1, wherein the adhesive material comprises a copolymer of caprolactone and glycolide (PCL/PGA).

Example 3

The surgical stapler end effector of Example 2, wherein the copolymer of PCL/PGA is provided at a ratio of 65/35.

Example 4

The surgical stapler end effector of Example 1, wherein the adhesive material comprises a copolymer of trimethylene carbonate and caprolactone (TMC/PCL).

Example 5

The surgical stapler end effector of Example 4, wherein the copolymer of TMC/PCL is provided at a ratio of 65/35.

Example 6

The surgical stapler end effector of Example 1, wherein the adhesive material comprises a copolymer of lactide and caprolactone (PLA/PCL).

Example 7

The surgical stapler end effector of Example 6, wherein the copolymer of PLA/PCL is provided at a ratio of 75/25.

Example 8

The surgical stapler end effector of Example 1, wherein the adhesive material comprises a copolymer of trimethylene carbonate and lactide (TMC/PLA).

Example 9

The surgical stapler end effector of any of the preceding or following Examples, wherein the adhesive material comprises an absorbable wax or putty.

Example 10

The surgical stapler end effector of Example 9, wherein the absorbable wax or putty comprises one or more of a water-soluble alkylene copolymer, glycerol, 1-lactide, glycolide, polyethylene glycol (PEG), polyethylene oxide (PEO), or polyolefin elastomer (POE).

Example 11

The surgical stapler end effector of Example 9, wherein the absorbable wax or putty comprises polyethylene glycol (PEG) or a polyethylene glycol (PEG) copolymer with a molecular weight of less than 20,000 g/mol.

Example 12

The surgical stapler end effector of any of the preceding or following Examples, wherein the adhesive material comprises oxidized regenerated cellulose (ORC).

Example 13

The surgical stapler end effector of any of the preceding or following Examples, wherein the adhesive layer is configured as a film on buttress body, wherein the film has a thickness in the range of 75 mils to 250 mils.

Example 14

The surgical stapler end effector of any of the preceding or following Examples, wherein the deck of the staple cartridge defines a plurality of openings, wherein the staple cartridge is operable to drive the staples through the openings of the deck, wherein the adhesive material defines a plurality of preformed openings, wherein the openings in the adhesive material are configured and arranged to correspond with the openings of the deck.

Example 15

The surgical stapler end effector of any of the preceding or following Examples, wherein the deck of the staple cartridge defines a plurality of openings, wherein the staple cartridge is operable to drive the staples through the openings of the deck, wherein the openings of the deck are arranged in rows, wherein the adhesive material comprises a plurality of rods, wherein the rods are configured and arranged to correspond with regions of the deck between the rows of openings.

Example 16

The surgical stapler end effector of any of the preceding or following Examples, wherein the adhesive material is configured and arranged in a plurality of discrete locations on the buttress body

Example 17

The surgical stapler end effector of any of the preceding or following Examples, further comprising a retainer, wherein the retainer comprises: (i) a holding surface configured to hold the buttress assembly, and (ii) a plurality of posts, wherein the posts are configured to provide focused pressure against discrete regions of the adhesive material to thereby drive the discrete regions of the adhesive material into engagement with the deck of the staple cartridge or the underside of the anvil.

Example 18

The surgical stapler end effector of Example 17, wherein the retainer further comprises a resilient member, wherein the resilient member is configured to resiliently urge the holding surface of the retainer into engagement with the deck of the staple cartridge or the underside of the anvil.

Example 19

A surgical stapler end effector, the end effector comprising: (a) a staple cartridge, wherein the staple cartridge comprises: (i) a plurality of staples, and (ii) a deck, wherein the deck defines a plurality of openings, wherein the staple cartridge is operable to drive the staples through the openings of the deck; (b) an anvil, wherein the anvil is movable from an open position toward the staple cartridge to reach a closed position, wherein the anvil includes an underside having staple forming surface configured to receive staples driven through the deck; and (c) a buttress assembly, wherein the buttress assembly comprises: (i) a buttress body, and (ii) an adhesive material, wherein the adhesive material is configured to removably secure the buttress body to the deck of the staple cartridge, wherein the adhesive material comprises defines openings or spaces configured to correspond with the openings of the deck to prevent the adhesive material from entering the openings of the deck.

Example 20

A surgical stapler end effector, the end effector comprising: (a) a staple cartridge, wherein the staple cartridge comprises: (i) a plurality of staples, and (ii) a deck, wherein the staple cartridge is operable to drive the staples through the deck; (b) an anvil, wherein the anvil is movable from an open position toward the staple cartridge to reach a closed position, wherein the anvil includes an underside having staple forming surface configured to receive staples driven through the deck; (c) a buttress assembly, wherein the buttress assembly comprises: (i) a buttress body, and (ii) an adhesive material, wherein the adhesive material is configured to removably secure the buttress body to the deck of the staple cartridge or the underside of the anvil; and (d) a retainer, wherein the retainer comprises: (i) a holding surface configured to hold the buttress assembly, and (ii) a plurality of protruding members, wherein the protruding members are configured to provide focused pressure against discrete regions of the adhesive material to thereby drive the discrete regions of the adhesive material into engagement with the deck of the staple cartridge or the underside of the anvil.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Mar. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No.9,301,759, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012; issued as U.S. Pat. No. 8,479,969, issued on Jul. 9, 2013, the disclosure of which is incorporated by reference herein; U.S. Pub. No. 2012/0138660, entitled "Robotically-Controlled Cable-Based Surgical End Effectors," published Jun. 7, 2012, issued as U.S. Pat. No. 8,800,838 issued on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler end effector, the end effector comprising:
   (a) a staple cartridge, wherein the staple cartridge comprises:
      (i) a plurality of staples, and
      (ii) a deck, wherein the deck defines a plurality of openings, wherein the staple cartridge is operable to drive the staples through the openings of the deck;
   (b) an anvil, wherein the anvil is movable from an open position toward the staple cartridge to reach a closed position, wherein the anvil includes an underside having staple forming surface configured to receive staples driven through the deck; and
   (c) a buttress assembly, wherein the buttress assembly comprises:
      (i) a buttress body, and
      (ii) a layer of adhesive material disposed on a surface of the buttress body, wherein the adhesive material is configured to removably secure the buttress body to the deck of the staple cartridge, wherein the adhesive material defines openings or spaces within the layer of adhesive material, wherein the openings or spaces in the layer of adhesive material are arranged to correspond in a one-to-one relationship with the openings of the deck.

2. The surgical stapler end effector of claim 1, wherein the adhesive material comprises a copolymer of caprolactone and glycolide (PCL/PGA).

3. The surgical stapler end effector of claim 2, wherein the copolymer of PCL/PGA is provided at a ratio of 65/35.

4. The surgical stapler end effector of claim 1, wherein the adhesive material comprises a copolymer of trimethylene carbonate and caprolactone (TMC/PCL).

5. The surgical stapler end effector of claim 4, wherein the copolymer of TMC/PCL is provided at a ratio of 65/35.

6. The surgical stapler end effector of claim 1, wherein the adhesive material comprises a copolymer of lactide and caprolactone (PLA/PCL).

7. The surgical stapler end effector of claim 6, wherein the copolymer of PLA/PCL is provided at a ratio of 75/25.

8. The surgical stapler end effector of claim 1, wherein the adhesive material comprises a copolymer of trimethylene carbonate and lactide (TMC/PLA).

9. The surgical stapler end effector of claim 1, wherein the adhesive material comprises an absorbable wax or putty.

10. The surgical stapler end effector of claim 9, wherein the absorbable wax or putty comprises one or more of a water-soluble alkylene copolymer, glycerol, 1-lactide, glycolide, polyethylene glycol (PEG), polyethylene oxide (PEO), or polyolefin elastomer (POE).

11. The surgical stapler end effector of claim 9, wherein the absorbable wax or putty comprises polyethylene glycol (PEG) or a polyethylene glycol (PEG) copolymer with a molecular weight of less than 20,000 g/mol.

12. The surgical stapler end effector of claim 1, wherein the adhesive layer is configured as a film on buttress body, wherein the film has a thickness in the range of 75 mils to 250 mils.

13. The surgical stapler end effector of claim 1, further comprising a retainer, wherein the retainer comprises:
    (i) a holding surface configured to hold the buttress assembly, and (ii) a plurality of posts, wherein the posts are configured to provide focused pressure against discrete regions of the adhesive material to thereby drive the discrete regions of the adhesive material into engagement with the deck of the staple cartridge or the underside of the anvil.

14. The surgical stapler end effector of claim 13, wherein the retainer further comprises a resilient member, wherein the resilient member is configured to resiliently urge the holding surface of the retainer into engagement with the deck of the staple cartridge or the underside of the anvil.

15. A surgical stapler end effector, the end effector comprising:
(a) a staple cartridge, wherein the staple cartridge comprises:
(i) a plurality of staples, and
(ii) a deck, wherein the staple cartridge is operable to drive the staples through the deck;
(b) an anvil, wherein the anvil is movable from an open position toward the staple cartridge to reach a closed position, wherein the anvil includes an underside having staple forming surface configured to receive staples driven through the deck; and
(c) a buttress assembly, wherein the buttress assembly comprises:
(i) a buttress body comprising a first lateral edge and a second lateral edge, wherein the first lateral edge and the second lateral edge define a first width therebetween,
(ii) a layer of adhesive material on a surface of the buttress assembly, wherein the layer of adhesive material comprises a third lateral edge and a fourth lateral edge, wherein the third lateral edge and the fourth lateral edge define a second width therebetween, wherein the adhesive material is configured to removably secure the buttress assembly to the deck of the staple cartridge or the underside of the anvil, wherein the adhesive material comprises a polymer, wherein the polymer is malleable, wherein the polymer is bioabsorbable, and
(iii) an intermediate layer interposed between the buttress body and the layer of adhesive material;
wherein the first width and the second width are equal.

16. The surgical stapler end effector of claim 15, wherein the adhesive material comprises oxidized regenerated cellulose (ORC).

17. The surgical stapler end effector of claim 15, wherein the deck of the staple cartridge defines a plurality of openings, wherein the staple cartridge is operable to drive the staples through the openings of the deck, wherein the adhesive material defines a plurality of preformed openings, wherein the openings in the adhesive material are configured and arranged to correspond with the openings of the deck.

18. The surgical stapler end effector of claim 15, wherein the deck of the staple cartridge defines a plurality of openings, wherein the staple cartridge is operable to drive the staples through the openings of the deck, wherein the openings of the deck are arranged in rows, wherein the adhesive material comprises a plurality of rods, wherein the rods are configured and arranged to correspond with regions of the deck between the rows of openings.

19. A surgical stapler end effector, the end effector comprising:
(a) a staple cartridge, wherein the staple cartridge comprises:
(i) a plurality of staples, and
(ii) a deck, wherein the staple cartridge is operable to drive the staples through the deck;
(b) an anvil, wherein the anvil is movable from an open position toward the staple cartridge to reach a closed position, wherein the anvil includes an underside having staple forming surface configured to receive staples driven through the deck;
(c) a buttress assembly, wherein the buttress assembly comprises:
(i) a buttress body, and
(ii) an adhesive material, wherein the adhesive material is configured to removably secure the buttress body to the deck of the staple cartridge or the underside of the anvil; and
(d) a retainer, wherein the retainer comprises:
(i) a holding surface configured to hold the buttress assembly, and
(ii) a plurality of protruding members on the holding surface, wherein the protruding members are configured to provide focused pressure in a direction perpendicular to and away from the holding surface against discrete regions of the adhesive material to thereby drive the discrete regions of the adhesive material into engagement with the deck of the staple cartridge or the underside of the anvil.

\* \* \* \* \*